Figure 1:
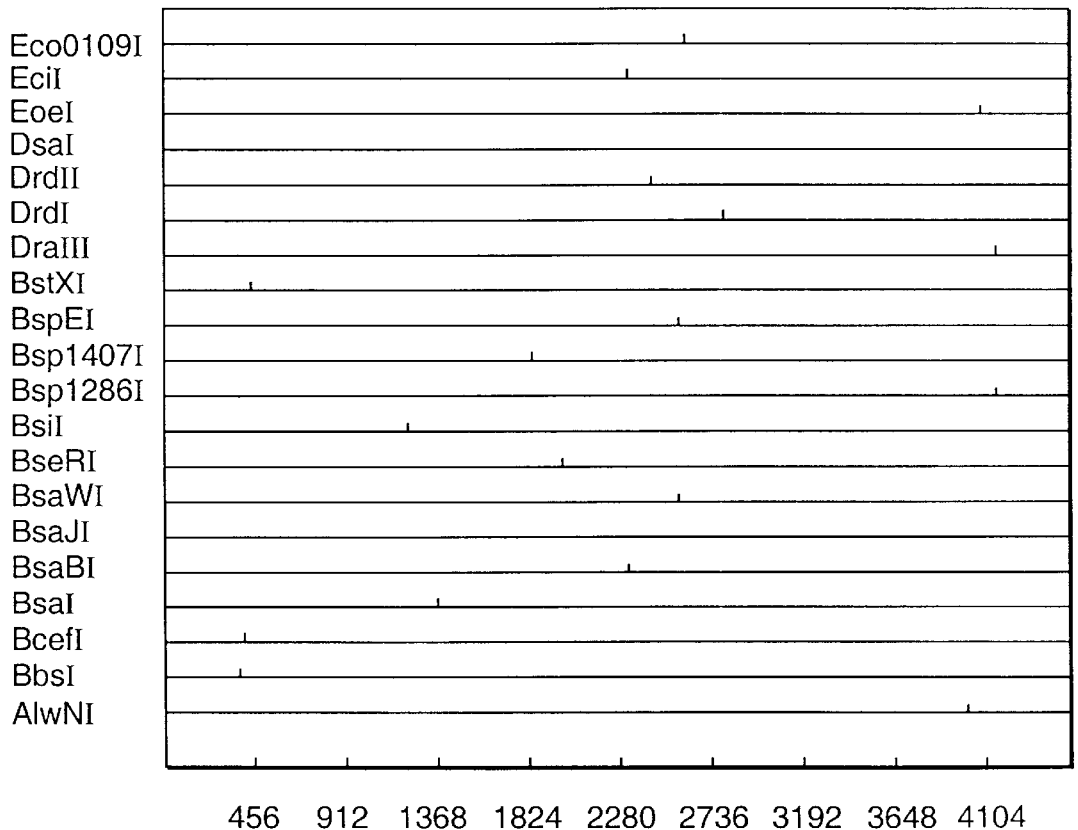

United States Patent [19]

Blanche et al.

[11] Patent Number: 6,001,631
[45] Date of Patent: Dec. 14, 1999

[54] TOPOISOMERASE IV, CORRESPONDING NUCLEOTIDE SEQUENCES AND USES THEREOF

[75] Inventors: Francis Blanche; Béatrice Cameron, both of Paris; Joël Crouzet, Sceaux; Alain Famechon, Janville-sur-Juine; Lucia Ferrero, Paris, all of France

[73] Assignee: Rhône-Poulenc Rorer S.A., Antony, France

[21] Appl. No.: 08/776,265

[22] PCT Filed: Jul. 26, 1995

[86] PCT No.: PCT/FR95/01001

§ 371 Date: Jan. 24, 1997

§ 102(e) Date: Jan. 24, 1997

[87] PCT Pub. No.: WO96/03516

PCT Pub. Date: Feb. 8, 1996

[30] Foreign Application Priority Data

Jul. 27, 1994 [FR] France .................................. 94 09288

[51] Int. Cl.⁶ .............................. C01N 9/90; C01N 1/20; C07H 21/04
[52] U.S. Cl. ................. 435/233; 435/252.3; 435/254.11; 435/320.1; 536/23.2
[58] Field of Search ................................ 435/233, 252.3, 435/254.11, 320.1; 536/23.2

[56] References Cited

PUBLICATIONS

Bagdasarian, M. et al., "Specific–purpose plasmid cloning vectors. II. broad host range, high copy number, RSF1010–derived vectors, and a host–vector system for gene cloning in Pseudomonas," Gene 16:237–247 (1981).

Ferrero et al., "Cloning and primary structure of *Staphylococcus aureus* DNA topoisomerase IV: a primary target fluoroquinolones," Molecular Microbiology 13(4):641–653 (1994).

Ferrero et al., "Analysis of gyrA and grlA Mutations in Stepwise–Selected Ciprofloxacin–Resistant Mutants of *Staphylococcus aureaus*," Antimicrobial Agents and Chemotherapy 39(7):1554–1558 (1995).

Gellert, M. et al. "DNA gyrase: An enzyme that introduces superhelical turns into DNA," Proc. Natl. Acad. Sci. USA 73:3872–3876 (1976).

Higgins, D.G. and Sharp, P.A., "CLUSTAL: a package for performing multiple sequence alignment on a microcomputer," Gene 73:237–244 (1988).

Holmes, M.L. and Dyall–Smith, M., "Mutations in DNA Gyrase Result in Novobiocin Resistance in Halophilic Archaebacteria," J. Bacteriol. 173(2):642–648 (1991).

Hopewell, R. et al., "DNA Cloning and Organization of the *Staphylococcus aureus* gyrA and gyrB Genes: Close Homology among Gyrase Proteins and Implications for 4–Quinolone Action and Resistance," J. Bacteriol., 172(6):3481–3484 (1990).

Hooper, D.C. and Wolfson, J.S., "Mechanisms of Quinolone Action and Bacterial Killing," In Quinolone Antimicrobial Agents, Hooper, D.C, and Wolfson, J.S. (eds), American Society of Microbiology, Washington, D.C., pp. 53–75 (1993).

Horowitz, D.S. and Wang, J.C., "Mapping the Active Site Tyrosine of *Escherichia coli* DNA Gyrase," J. Biol. Chem. 262(11):5339–5344 (1987).

Kato, J. et al., "Purification and Characterization of DNA Topoisomerase IV in *Escherichia coli*," J. Biol. Chem. 267(36):25676–25684 (1992).

Kato, J. et al., "New Topoisomerase Essential for Chromosome Segregation in *E. coli*," Cell 63(2):393–404 (1990).

Luttinger, A.L. et al., "A Cluster of Genes That Affects Nucleoid Segregation in *Salmonella typhimurium*," New Biol 3:(7)687–697 (1991).

Margerrison, E.E.C. et al., "Nucleotide Sequence of the *Staphylococcus aureus* gyrB–gyrA Locus Encoding the DNA Gyrase A and B Proteins," J. Bacteriol., Am. Soc. Microbiol., 174(5):1596–1603 (1992).

Ng E. Y. et al., "Novel Mutations in Topoisomerase IV (Topo4) in Quinolone–Resistant (OR) flgA Mutants and Their Interaction with OR gyrA Mutations in *Staphylococcus aureus*," 95th General Meeting of the American Society for Microbiology, Washington, D.C., May 21–25, 1995. Abstracts General Meeting of the American Society for Microbiology 95(0) (1995).

Normark, S. et al., "Overlapping Genes," Ann. Rev. Genet. 17:499–525 (1983).

Novick, R.P., "The Staphylococcus as a Molecular Genetic System," in Molecular Biology of the Staphyloccoci, Novic, R.P. (ed). VCH Publishers, Inc., New York, pp. 1–37 (1990).

H. Peng and K. J. Marians, "*Escherichia coli* Topoisomerase IV," J. Biol. Chem. 268(32):24481–24490 (1993).

H. Peng and K. J. Marians, "Decatenation activity of topoisomerase IV during oriC and pBR322 DNA replication in vitro," Proc. Natl. Acad. Sci. 90:8571–8575 (1993).

Sreedharan S. et al., "DNA Gyrase gyrA Mutations in Ciprofloxacin–Resistant Strains of *Staphylococcus aureus*: Close Similarity with Quinolone Resistance Mutations in *Escherichia coli*," J. Bacteriol., 172(12):7260–7262 (1990).

Staudenbauer, W.L. and Orr, E., "DNA gyrase: affinity chromatography on novobiocin–Sepharose and catalytic properties," Nucleic Acid Reserach, 9(15):3589–3603 (1981).

Studier, W.F. et al., "Use of T7 RNA Polymerase to Direct Expression of Cloned Genes," Methods In Enzymol. 185:60–89 (1990).

Wigley, D.B. et al., "Crystal structure of an N–terminal fragment of the DNA gyrase B protein," Nature 351:624–629 (1991).

*Primary Examiner*—Robert A. Wax
*Attorney, Agent, or Firm*—Finnegan, Henderson, Farabow, Garrett & Dunner, L.L.P.

[57] ABSTRACT

A novel topoisomerase IV, nucleotide sequences coding for said enzyme, corresponding vectors, and the use of said enzyme for screening biologically active materials.

17 Claims, 6 Drawing Sheets

TOPOISOMERASE IV, CORRESPONDING NUCLEOTIDE SEQUENCES AND USES THEREOF

The present invention relates to a novel topoisomerase IV, the nucleotide sequences encoding this enzyme, their corresponding vectors and the use of this enzyme for screening biologically active products.

Topoisomerases are enzymes capable of modifying the topological configuration of DNA rings, of making knots therein or of interlacing separated rings. They are thus involved in the replication, transcription and recombination of the entire genetic information (Wang et al., 1990). The mechanism of all these topological conversions is the same: the ring is opened so that a segment of DNA passes through the gap before the ends are rejoined. Two types of topoisomerase are involved in these conversions: type I topoisomerases which cut a single DNA strand and type II topoisomerases which cut both strands simultaneously.

Up until now, two type II bacterial topoisomerases have been identified and studied more particularly: gyrase from *Escherichia coli* (Gellert et al., 1976), and more recently, DNA topoisomerase IV from *E. coli* (Kato et al., 1990).

Gyrase is a $\alpha_2\beta_2$ tetramer whose $\alpha$ or GyrA and $\beta$ or GyrB subunits are encoded by the gyrA and gyrB genes respectively. Bacterial gyrases are the only known topoisomerases capable of supercoiling relaxed DNA rings in the presence of ATP.

As regards more particularly DNA topoisomerase IV from *E. coli*, it relaxes supercoiled plasmid DNA, unknots T4 phage DNA and unwinds (or decatenates) kinetoplast DNA (Kato et al., 1992; Peng et al., 1993). The sequence of its corresponding genes, parC and parE from *E. coli*, has made it possible to demonstrate regions of high similarity between the subunits of gyrase and those of this topoisomerase IV, ParC with GyrA (35.6% over the entire sequence) and ParE with GyrB (40.1% over the entire sequence) respectively (Kato et al., 1990).

*E. coli* gyrase has also been identified as being a primary target of fluoroquinolones (Hooper et al., 1993). It has thus been demonstrated that *E. coli* strains mutated at the level of the Ser83 residue in the GyrA subunit have a high resistance to fluoroquinolones (Maxwell, 1992). Fluoroquinolones bind less to DNA-mutated gyrase complexes than to DNA-wild-type gyrase complexes. Indeed, other point mutations, mapped in the region between residues 67 and 106 of GyrA, lead to strains resistant to fluoroquinolones. This region is called QRDR (Yoshida et al., 1990; Cullen et al., 1989). Similar results have been published with strains of *Staphylococcus aureus* resistant to fluoroquinolones (Goswitz et al., 1992; Sreedharan et al., 1990). Gyrase is therefore nowadays recognized as being the primary target of quinolones. However, a clinical strain of *Staphylococcus aureus*, not containing any mutation in the QRDR region of GyrA, has also been described as resistant to fluoroquinolones (Sreedharan et al., 1991).

Nowadays, this phenomenon of resistance developed by *Staphylococcus aureus* bacteria towards antibiotics and more particularly towards fluoroquinolones is being increasingly encountered at the therapeutic level. It would be particularly important to be able to lift this resistance and this involves a characterization of all the parameters which are associated with it.

The main objective of the present invention is precisely the identification, sequencing and characterization of nucleic sequences encoding subunits of a novel topoisomerase, topoisomerase IV of *Staphylococcus aureus*, composed of two subunits, GrlA and GrlB.

Unexpectedly, the applicant has found that the primary target of the fluoroquinolones in *S. aureus* is a topoisomerase IV and not gyrase. It has thus demonstrated that clinical strains of *S. aureus*, in which the QRDR region of the GyrA subunit of gyrase is identical to the wild-type sequence, develop nevertheless a resistance to fluoroquinolones because of a mutation which they possess in the region of the GrlA subunit of topoisomerase IV, homologous to the QRDR region.

The first subject of the present invention is a nucleotide sequence encoding at least one subunit of topoisomerase IV of *Staphylococcus aureus*.

The present invention describes in particular the isolation and the characterization of the grlA and grlB genes. These genes have been cloned, sequenced and expressed in *E. coli*, and their enzymatic activity has been characterized. They were isolated from a *Staphylococcus aureus* genomic DNA library. From the grlAB nucleic sequence (SEQ ID NO:1 and SEQ ID NO:2), two open frames, corresponding to the grlB and grlA genes respectively, have been identified. The grlA and grlB genes have been sequenced in (SEQ ID NO:4) and (SEQ ID NO:6) respectively.

Preferably, the subject of the present invention is a nucleotide sequence chosen from:

(a) all or part of the grlA (SEQ ID NO:4) or grlB (SEQ ID NO:6) genes, (b) the sequences hybridizing with all or part of the (a) genes and encoding a subunit of a topoisomerase IV, and (c) the sequences derived from the (a) and (b) sequences because of the degeneracy of the genetic code.

It is clear that from the genes identified in the present application, it is possible, by hybridization, to directly clone other genes encoding a subunit of topoisomerase IV of bacteria close to *S. aureus* such as for example Streptococci and Enterococci. It is thus possible to clone this type of gene using, as probe, the genes grlA, grlB or fragments thereof. Likewise, the cloning of these genes may be carried out using degenerate oligonucleotides derived from sequences of the grlA or grlB genes or fragments thereof.

For the purposes of the present invention, derivative is understood to mean any sequence obtained by one or more modifications and encoding a product conserving at least one of the biological properties of the original protein. Modification should be understood to mean any mutation, substitution, deletion, addition or modification of a genetic and/or chemical nature. These modifications may be performed by techniques known to persons skilled in the art.

Among the preferred derivatives, there may be mentioned more particularly natural variants, molecules in which one or more residues have been substituted, derivatives obtained by deletion(s) of regions not or little involved in the interaction between the binding sites considered or expressing an undesirable activity, and derivatives having, compared with the native sequence, one or more additional residues.

Still more preferably, the subject of the invention is the nucleotide sequences represented by the grlA (SEQ ID NO:4) and grlB (SEQ ID NO:6) genes.

It also relates to any grlA gene having a mutation leading to a resistance to molecules of the quinolone and more particularly of the fluoroquinolone family. As a representative of these mutated genes, there may be mentioned more particularly the grlA gene having a base change from C to A at position 2270 of SEQ ID NO:4. The resulting gene is termed $grlA_{(C-2270A)}$. This mutation leads to substitution of the Ser-80 residue with Tyr in the GrlA protein. The resulting protein will be designated by $GrlA_{(Ser-80\ Tyr)}$.

Another subject of the present invention relates to a recombinant DNA comprising at least one nucleotide sequence encoding a subunit of topoisomerase IV of *Staphylococcus aureus*. More preferably, it is a recombinant DNA comprising at least one nucleotide sequence as defined above in (a), (b) and (c) and more particularly the gene grlA (SEQ ID NO:4) grlA$_{(C-2270A)}$ and/or the gene grlB (SEQ ID NO:6).

According to a preferred mode of the invention, the nucleotide sequences defined above form part of an expression vector which may be autonomously replicating or integrative.

Another subject of the invention relates to the polypeptides resulting from the expression of the nucleotide sequences as defined above. More particularly, the present invention relates to the polypeptides comprising all or part of the polypeptides GrlA (SEQ ID NO:3) or GrlB (SEQ ID NO:5) or of their derivatives. For the purposes of the present invention, the term derivative designates any molecule obtained by modification of the genetic and/or chemical nature of the peptide sequence. Modification of the genetic and/or chemical nature may be understood to mean any mutation, substitution, deletion, addition and/or modification of one or more residues. Such derivatives may be generated for different purposes, such as especially that of increasing the affinity of the peptide for its substrate(s), that of enhancing its production levels, that of increasing its resistance to proteases, that of increasing and/or of modifying its activity, or that of conferring new biological properties on it. Among the derivatives resulting from an addition, there may be mentioned, for example, the chimeric polypeptides containing an additional heterologous part attached to one end. The term derivative also comprises the polypeptides homologous to the polypeptides described in the present invention, derived from other cellular sources.

Preferably, they are the polypeptides GrlA (SEQ ID NO:3), GrlB (SEQ ID NO:5) and GrlA$_{(Ser-80\ Tyr)}$.

The subject of the invention is also any recombinant cell containing a nucleotide sequence, a recombinant DNA and/or a vector as defined above. The recombinant cells according to the invention may be both eukaryotic and prokaryotic cells. Among the suitable eukaryotic cells, there may be mentioned animal cells, yeasts, or fungi. In particular, as regards yeasts, there may be mentioned yeasts of the genus Saccharomyces, Kluyveromyces, Pichia, Schwanniomyces or Hansenula. As regards animal cells, there may be mentioned COS, CHO and C127 cells, Xenopus eggs, and the like. Among the fungi, there may be mentioned more particularly Micromonospora, Aspergillus ssp. or Trichoderma ssp. Preferably, they are prokaryotic cells. In this case, the following bacteria may be more particularly used: Actinomycetes, Bacillus, and more preferably *E. coli* and Staphylococcus. The recombinant cells of the invention may be obtained by any method allowing the introduction of a foreign nucleotide sequence into a cell. This may be especially transformation, electroporation, conjugation, fusion of protoplasts, or any other technique known to persons skilled in the art.

The subject of the present invention is also a process for the preparation of polypeptides as claimed from the culture of one of these recombinant cells. The polypeptide(s) thus obtained are recovered according to conventional methods after the culture.

The invention also relates to an isolated topoisomerase IV capable of being obtained from the expression of all or part of the grlA gene (SEQ ID NO:4) and of all or part of the grlB gene (SEQ ID NO:6) or of their respective derivatives.

Derivative is understood to designate the sequences hybridizing with all or part of the grlA or grlB gene and encoding a subunit of a topoisomerase IV as well as all the sequences derived from a degeneracy of the genetic code of these hybrid sequences or of the sequences corresponding to all or part of the grlA or grlB gene.

More preferably, it is an isolated topoisomerase IV derived from the expression of all or part of the grlA gene (SEQ ID NO:4) or of all or part of the grlB gene (SEQ ID NO:6).

The present invention relates more particularly to any topoisomerase IV behaving as a primary target towards fluoroquinolones.

According to a specific mode of the invention, it is topoisomerase IV of *Staphylococcus aureus*.

The claimed topoisomerase IV according to the invention is most particularly useful for targeting biologically active products such as for example potential antibiotics and especially molecules of the fluoroquinolone family. Advantageously, it may also be used to assay and/or identify products inhibiting the ATP-dependent DNA relaxing reaction and/or the products inhibiting the reaction of decatenation of catenanes of DNA.

The applicant has thus developed an assay for enzymatic activity which is specific for topoisomerase IV of *S. aureus* and has shown that this activity is inhibited by antibiotic molecules such as fluoroquinolones.

The present invention provides a new target for searching for new antibiotics, as well as a screen specific for this target; this screen is described in Example 7. This screen makes it possible to demonstrate the products which inhibit DNA topoisomerase IV of *S. aureus*. The following may be used in this test: pure or mixed synthetic products, natural plant extracts, bacterial cultures, fungi, yeasts or algae, pure or in the form of a mixture. The test described in the present invention makes it possible to detect both products which stabilize the cleavable complex, a reaction intermediate of the reaction catalysed by the enzyme, and also inhibitors acting through other mechanisms.

The examples and figures presented below by way of nonlimiting illustration show other advantages and characteristics of the present invention.

LEGEND TO THE FIGURES

FIG. 1: Restriction map of the 4565 bp fragment containing the grlB and grlA genes of *S. aureus*.

Figure 2A:
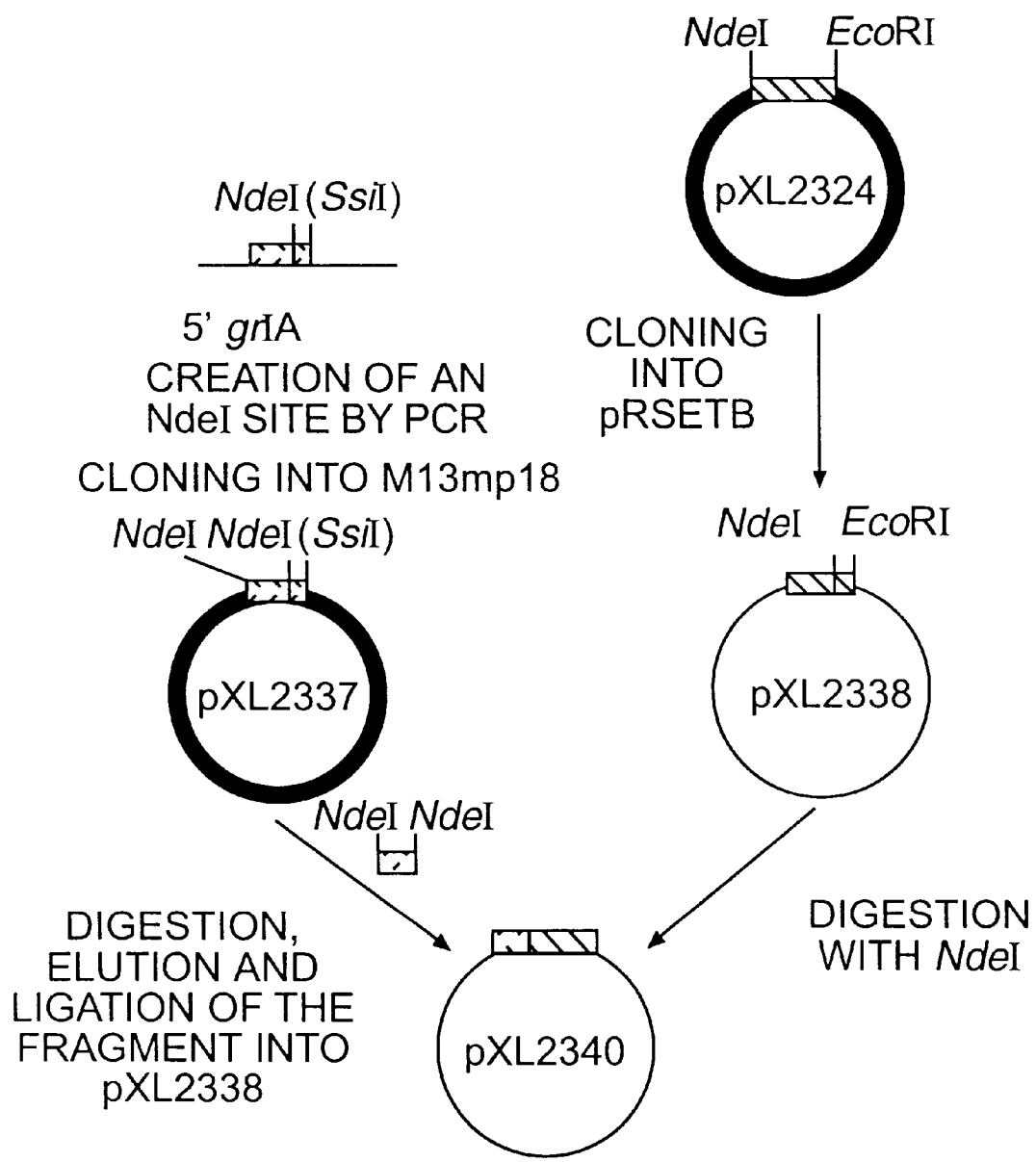
Figure 2B:
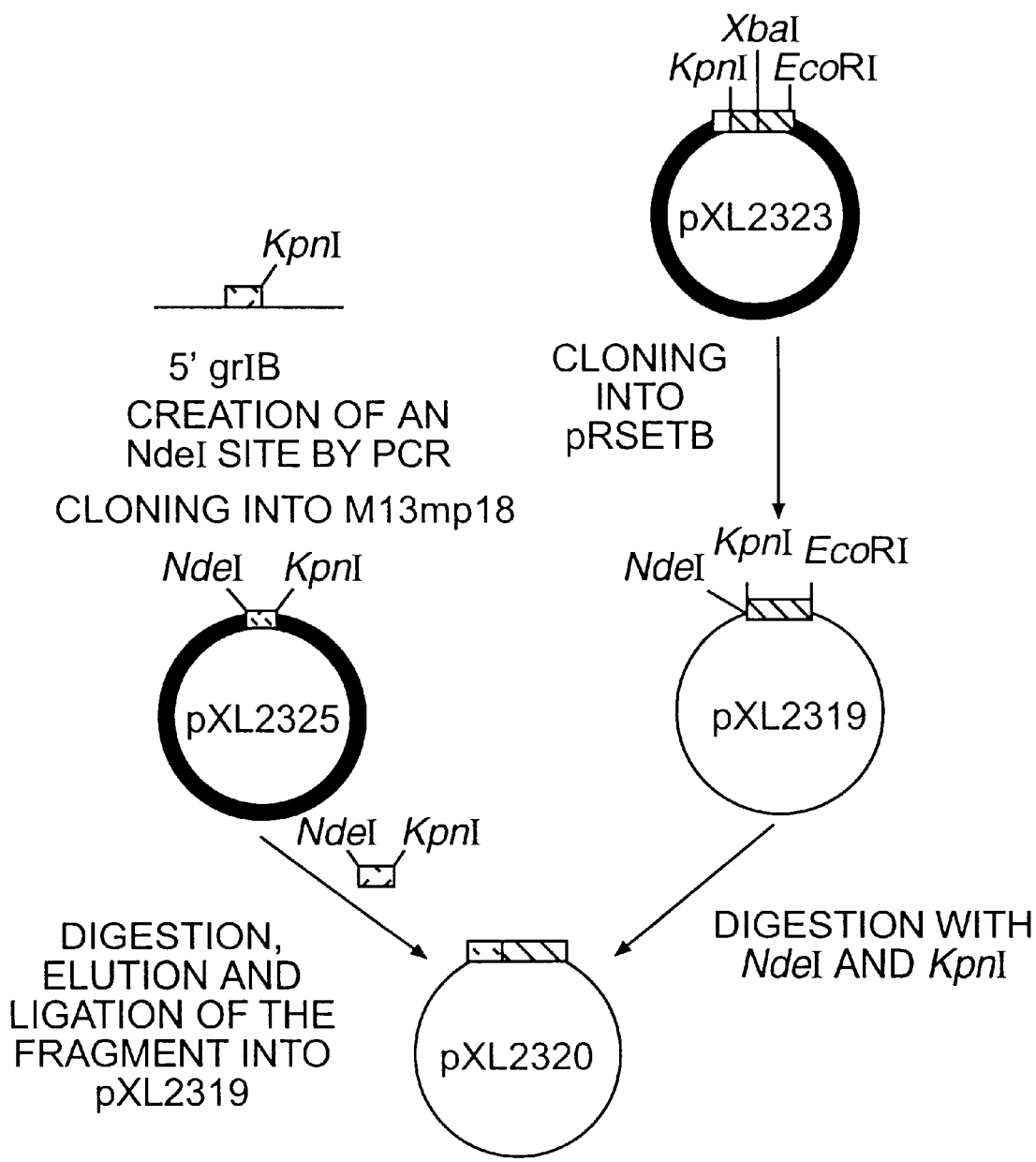

FIGS. 2A and 2B: Construction of the plasmids for expression of grlA and grlB. The constructs produced with grlA are schematically represented in A and those of grlB are in B. The cloned *S. aureus* DNA is represented by the shaded rectangles, the vectors derived from M13 are in a thick black line and the expression vectors are in a fine black line, the SstI restriction site is in brackets because it is a cloning site.

Figure 3:
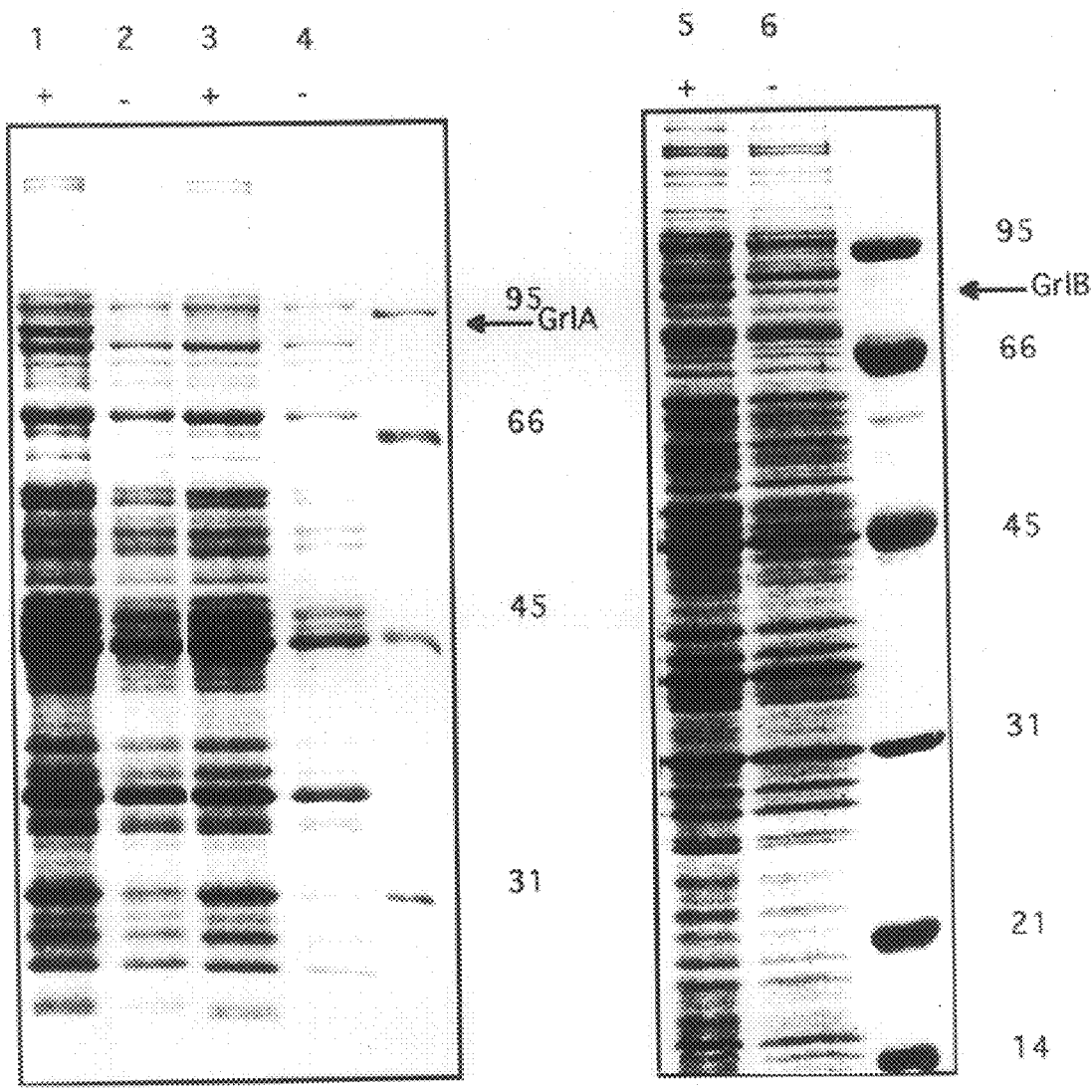

FIG. 3: PAGE-SDS electrophoresis gel stained with Coomasie blue. Total cell extracts are deposited, lanes: 1 and 2, XL1-blue, pXL2340; 3 and 4, XL1-blue, pRSETB; 5 and 6, XL1-blue, pXL2320. The molecular weight markers (in hundreds) are indicated on the right of the figure. The arrow shows the overproduced protein. The + or − signs represent the induction with or without IPTG.

Figure 4:
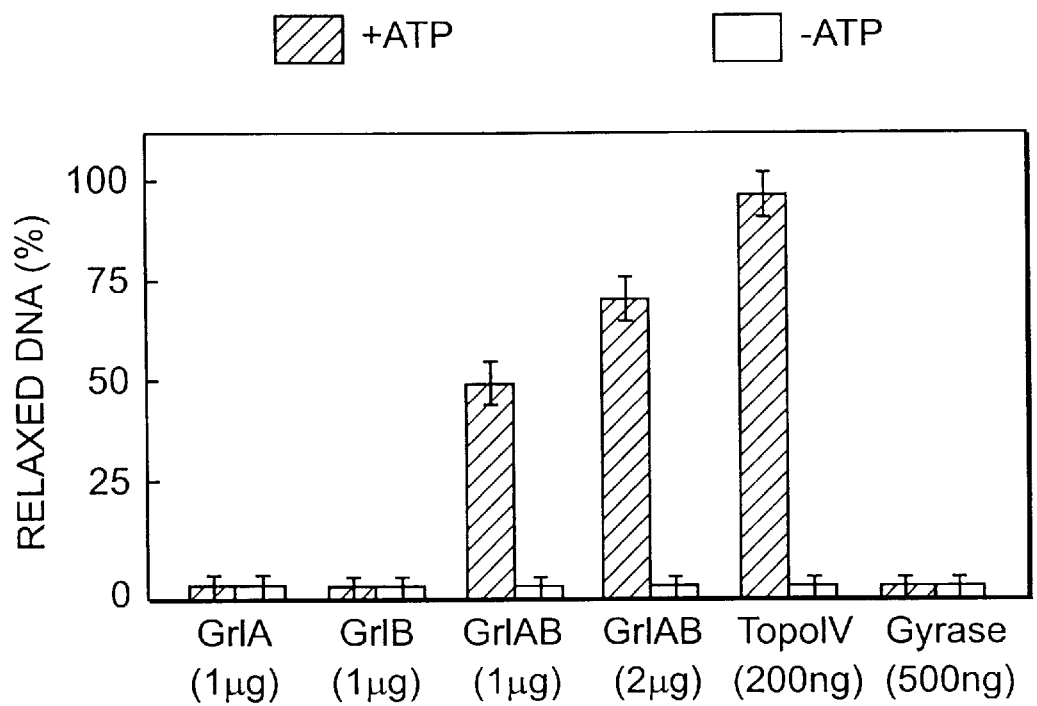

FIG. 4: ATP-dependent relaxation activity of the GrlAB protein. The control experiments with purified DNA topoisomerase IV of *E. coli* (Peng and Marians, 1993) and purified DNA gyrase of *E. coli* (Hallet et al., 1990) are also described.

Figure 5:

FIG. 5: Decatenation activity of the protein GrlAB. kDNA, kinetoplast DNA; monomers, relaxed and decatenated DNA monomers. TopoIV: purified DNA topoisomerase IV of *E. coli* (50 ng); Gyrase: purified DNA gyrase of *E. coli* (50 ng); GrlA: GrlA protein extract (2 μg); GrlB: GrlB protein extract (2 μg); GrlAB: GrlA protein extract (2 μg) mixed with the GrlB protein extract (2 μg).

EXAMPLE 1
PCR Amplification of DNA Fragments of *Staphylococcus aureus* which are Inside the GrlA and GrlB Genes This example describes the production of DNA fragments of *Staphylococcus aureus* which are inside the grlA and grlB genes. These fragments were obtained after PCR amplification carried out at 50° C. with genomic DNA of the *Staphylococcus aureus* strain RN4220 (Novick, 1990) and of the degenerate oligonucleotides corresponding to the amino acids conserved in the N-terminal regions of the subunits GyrA of *E. coli* and *B. subtilis* and ParC of *E. coli* or of the subunits GyrB of *E. coli* and *B. subtilis* and ParE of *E. coli*. More specifically, the sense oligonucleotides 2137 and antisense oligonucleotides 2135 made it possible to amplify fragments of 255 bp which can encode 85 amino acids which would correspond to positions 39 to 124 on the *E. coli* GyrA sequence; the sequence of the sense oligonucleotide 2137 is 5'-GCGC GAATTCGATGG(A,T)(C,T)T-(A,T)AAACC(A,T)GT-(A,T)CA-3' (SEQ ID NO:7) and that of the antisense 2135 is 5'-CGCGAAGCTTTTC(T,A)GTATA(A,T)C-(T,G)CAT(A,T)GC- (A,T)GC-3' (SEQ ID NO:8). The oligonucleotides 2144 and 2138 led to the amplification of 1 kb fragments which can encode 333 amino acids which would correspond to positions 98 to 430 on the *E. coli* GyrB sequence; the sequence of the sense oligonucleotide 2144 is 5'-GCGC GAATTCT(T,A)CATGC(A,T)-GG(T,A)GG(T,A)AAATT-3' (SEQ ID NO:9), and that of the antisense 2138 is 5'-CGCG AAGCTT(T,A)CC(T,A)CC(T,A)GC-(T,A)GAATC(T,A)-CCTTC-3' (SEQ ID NO:10). The fragments were cloned and a total of 40 clones were analysed by sequencing their insert. The sequence of the oligonucleotides used for the PCR was found for 31 clones out of 40; among the 31 clones, 20 have a sequence which is inside the gyrA or gyrB gene of *S. aureus;* the other 11 clones contain either a fragment A of 255 bp or a fragment B of 1 kb.

The amino acid sequence which the A fragment is thought to encode has 59% identity with the GyrA subunit of *S. aureus* between positions 44 to 125, the A fragment is therefore thought to be part of an *S. aureus* grlA gene thus newly identified. Likewise, the amino acid sequence which the B fragment is thought to encode has 51% identity with the GyrB subunit of *S. aureus* between positions 105 to 277, the B fragment is therefore thought to be part of an *S. aureus* grlB gene thus newly identified.

EXAMPLE 2
Cloning and Sequencing of the grlA and grlB Genes of *Staphylococcus aureus*

This example describes the molecular biology experiments which have made it possible to clone and then sequence the grlA and grlB genes of *Staphylococcus aureus*.

The A and B fragments described in Example 1 were used as radioactive probe to identify, by hybridization, the grlA and grlB genes in a genomic DNA library of *S. aureus* FDA 574 (CE ent⁺) constructed in λgt11 by Clontech Laboratories (catalogue XL1501b, batch 0721). Out of a total of 250,000 recombinant phages, twelve phages hybridize with the A fragment or the B fragment but do not hybridize with oligonucleotides specific for the gyrA or gyrB genes. The size of the EcoRI inserts contained in these phages varies between 0.7 and 3.5 kb and two phages, 16 and 111, whose insert is of a larger size, were studied. The EcoR1 insert of 3.5 kb of the phage 16 was eluted and then digested with XbaI and the two fragments of 1.5 and 2 kb were cloned into M13mp19 and M13mp18 (Boehringer Mannheim) in order to generate pXL2321 and pXL2322. Likewise, the EcoRI insert of 3.6 kb of the phase 111 was eluted and then digested with PstI and the 2 kb fragment was cloned into M13mp19 in order to generate pXL2324.

The inserts contained in the recombinant phages pXL2321, pXL2322 and pXL2324 were sequenced on both strands with the aid of the universal primer or of internal oligonucleotides using the Sanger method. The nucleic sequence grlAB (SEQ ID NO:1 and SEQ ID NO:2) of 4565 bp was analysed with the programme by Staden et al., 1982 in order to identify the coding sequences with the aid of a codon usage table for *S. aureus*. Only two open frames ORF1 (positions 41 to 2029) and ORF2 (positions 2032 to 4431) were thus determined. In SEQ ID NO:1, which is the coding strand, starts arbitrarily at ATG position 41 but it can also start at TTG position 17 or 35, this codon being already described as initiation codon in *S. aureus;* the stop codon of ORF1 overlaps with the initiation codon GTG of ORF2, which is characteristic of a translational coupling (Normark et al., 1983); such a coupling has, for example, been described for the gyrA and gyrB genes of *Haloferax* sp. (Holmes et al., 1991). These open frames have a percentage of GC of 34.5% which is a value in agreement with the values described for the *S. aureus* DNA in the literature (Novick, 1990). Moreover, the B fragment is identical to the sequence described on SEQ ID No. 1 from position 333 to position 1348 in ORF1 and the fragment A is identical to the sequence of SEQ ID No. 1 from position 2137 to position 2394 in ORF2. From the nucleotide sequence, a restriction map is produced with enzymes which cut least frequently, see FIG. 1.

This sequence analysis shows that ORF1 is the grlB gene and ORF2 the grlA gene.

EXAMPLE 3
Primary Structure, Expression and Function of the GrlA and GrlB Proteins Encoded by the grlA and grlB Genes of *Staphylococcus aureus*

This example describes the primary structure, the expression in *E. coli* and the function of the GrlA and GrlB proteins of *Staphylococcus aureus*. This function, which corresponds to a DNA topoisomerase IV, is based, in this example, on sequence homology and genetic complementation data.

3.1—Primary Structure and Sequence Analysis of the GrlA and GrlB Proteins

This example describes computer analysis of the sequence of the grlA and grlB genes of *Staphylococcus aureus* carried out using the sequence data presented in Example 2. The grlB gene encodes a GrlB protein of 663 amino acids (molecular weight 74,318), and the grlA gene encodes a GrlA protein of 800 amino acids (molecular weight 91,040). The coding parts of the grlB and grlA genes, the sequences of the GrlB and GrlA proteins are presented in SEQ ID NO:5 and SEQ ID NO:3 respectively and the properties of each of these proteins (amino acid composition, isoelectric point, polarity index) are presented in Tables 1 and 2 below.

| Protein: GrlA: | |
|---|---|
| First residue = 1 and last residue | = 800 |
| Molecular mass (monoisotopic) | = 91040.8438 |
| Molecular mass (average) | = 91097.2578 |

-continued

Protein: Gr1A:

| | |
|---|---|
| Polarity index (%) | = 52.00 |
| Isoelectric point | = 6.77 |
| OD 260 (1 mg/ml) = 0.298 | OD 280 (1 mg/ml) = 0.487 |

TABLE 1

| | | | NUMBER | % NOMB | WEIGHT | % WEIGHT |
|---|---|---|---|---|---|---|
| 1 | Phe | F | 22 | 2.75 | 3235.51 | 3.55 |
| 2 | Leu | L | 74 | 9.25 | 8368.22 | 9.19 |
| 3 | Ile | I | 77 | 9.63 | 8707.47 | 9.56 |
| 4 | Met | M | 19 | 2.38 | 2489.77 | 2.73 |
| 5 | Val | V | 59 | 7.38 | 5845.04 | 6.42 |
| 6 | Ser | S | 51 | 6.38 | 4438.63 | 4.88 |
| 7 | Pro | P | 22 | 2.75 | 2135.16 | 2.35 |
| 8 | Thr | T | 43 | 5.38 | 4345.05 | 4.77 |
| 9 | Ala | A | 37 | 4.63 | 2628.37 | 2.89 |
| 10 | Tyr | Y | 28 | 3.50 | 4565.77 | 5.02 |
| 12 | His | H | 20 | 2.50 | 2741.18 | 3.01 |
| 13 | Gln | Q | 26 | 3.25 | 3329.52 | 3.66 |
| 14 | sn | N | 45 | 5.63 | 5131.93 | 5.64 |
| 15 | Lys | K | 66 | 8.25 | 8454.27 | 9.29 |
| 16 | Asp | D | 54 | 6.75 | 6211.45 | 6.82 |
| 17 | Glu | E | 67 | 8.38 | 8645.85 | 9.50 |
| 18 | Cys | C | 0 | 0.00 | 0.00 | 0.00 |
| 19 | Trp | W | 2 | 0.25 | 372.16 | 0.41 |
| 20 | Arg | R | 44 | 5.50 | 6868.45 | 7.54 |
| 21 | Gly | G | 44 | 5.50 | 2508.94 | 2.76 |

GrlB protein:

| | |
|---|---|
| First residue = 1 and last residue = | 663 |
| Molecular mass (monoisotropic) = | 74318.3516 |
| Molecular mass (average) = | 74363.9219 |
| Polarity index (%) = | 53.70 |
| Isoelectric point = | 7.21 |
| OD 260 (1 mg/ml) = 0.404 OD 280 (1 mg/ml) = | 0.603 |

TABLE 2

| | | | NUMBER | % NOMB | WEIGHT | % WEIGHT |
|---|---|---|---|---|---|---|
| 1 | Phe | F | 26 | 3.92 | 3823.78 | 5.15 |
| 2 | Leu | L | 55 | 8.30 | 6219.62 | 8.37 |
| 3 | Ile | I | 36 | 5.43 | 4071.03 | 5.48 |
| 4 | Met | M | 10 | 1.51 | 1310.40 | 1.76 |
| 5 | Val | V | 50 | 7.54 | 4953.42 | 6.67 |
| 6 | Ser | S | 41 | 6.18 | 3568.31 | 4.80 |
| 7 | Pro | P | 15 | 2.26 | 1455.79 | 1.96 |
| 8 | Thr | T | 41 | 6.18 | 4142.95 | 5.57 |
| 9 | Ala | A | 33 | 4.98 | 2344.22 | 3.15 |
| 10 | Tyr | Y | 19 | 2.87 | 3098.20 | 4.17 |
| 12 | His | H | 14 | 2.11 | 1918.82 | 2.58 |
| 13 | Gln | Q | 26 | 3.92 | 3329.52 | 4.48 |
| 14 | Asn | N | 36 | 5.43 | 4105.55 | 5.52 |
| 15 | Lys | K | 63 | 9.50 | 8069.98 | 10.86 |
| 16 | Asp | D | 40 | 6.03 | 4601.08 | 6.19 |
| 17 | Glu | E | 61 | 9.20 | 7871.60 | 10.59 |
| 18 | Cys | C | 0 | 0.00 | 0.00 | 0.00 |
| 19 | Trp | W | 4 | 0.60 | 744.32 | 1.00 |
| 20 | Arg | R | 34 | 5.13 | 5307.44 | 7.14 |
| 21 | Gly | G | 59 | 8.90 | 3364.27 | 4.53 |

The Kanehisa programme, described in 1984, was used to align the GrlB and GrlA proteins with the following type II bacterial DNA topoisomerases, the *E. coli, B. subtilis* or *S. aureus* gyrases or the *E. coli* topoisomerase IV. The degrees of identity, see Table 3, are high and are between 32 and 55%. More specifically, GrlB exhibits a greater degree of identity with the GyrB subunits of *E. coli* (49%) and of *S. aureus* (52%) than with ParE of *E. coli* (38%), whereas GrlA exhibits comparable degrees of identity with the GyrA subunits of *E. coli* (32%) and of *S. aureus* (39%) than with ParE of *E. coli* (33%).

The GyrB subunits of *Staphylococcus aureus* (Margerrison et al., 1992), *Bacillus subtilis* (Moriya et al., 1985), and *Escherichia coli* (Adachi et al., 1987) are called SAGYRB, BSGYRB and ECGYRB respectively, GrlB is called SAGRLB and ECPARE corresponds to ParE of *E. coli* (Kato et al., 1990). A similar nomenclature is used for the GyrA, GrlA and ParC subunits. The numbers under the name of the proteins are the numbers of amino acids in them.

TABLE 3

| B or B-like subunits | SAGYRB 644 | SAGRLB 663 | BSGYRB 638 | ECGYRB 804 |
|---|---|---|---|---|
| SAGRLB | 52% | | | |
| BSGYRB | 68% | 55% | | |
| ECGYRB | 55% | 49% | 57% | |
| ECPARE | 40% | 38% | 40% | 40% |
| A or A-like subunits | SAGYRA 887 | SAGRLA 800 | BSGYRA 821 | ECGYRA 875 |
| SAGRLA | 39% | | | |
| BSGYRA | 65% | 40% | | |
| ECGYRA | 39% | 32% | 41% | |
| ECPARC | 38% | 33% | 36% | 32% |

Multiple alignments between the type II bacterial topoisomerases, performed with the CLUSTAL programme of Higgins et al., 1988, show numerous conserved regions between the sequences of the various B, GrlB and ParE subunits and in the N-terminal part of the sequence of the A, GrlA and ParC subunits. The residues conserved in the N-terminal region of the B subunits of these proteins are in fact the residues involved in the binding of ATP and identified from X-ray crystallization data with the *E. coli* GyrB (Wigley et al., 1991). The residues conserved in the N-terminal region of the A subunits of these proteins are either the residues AAMRYTE (SEQ ID NO:11) close to the active site of gyrase Tyr-122, identified on the *E. coli* GyrA (Horowitz et al., 1987), or the residues YHPHGDS (SEQ ID NO:12) modified in the strains resistant to fluoroquinolones (Hooper et al., 1993).

3.2—Expression of the grlA and grlB Genes in *E. coli*

This example describes the constructs produced in order to express, in *E. coli*, the grlA or grlB genes under the control of the pT7 promoter (Studier et al., 1990). The expression plasmid pXL2320, see FIG. 2, containing the grlB gene in the vector pRSETB (Studier et al., 1990; Invitrogen) was constructed by cloning 1) the 1 kb EcoRI-XbaI insert of pXL2321 into pXL2322 at the XbaI and EcoRI sites in order to generate pXL2323; 2) the 1.9 kb KpnI-EcoRI insert of pXL2323 at the KpnI and EcoRI sites of the vector pRSETB in order to generate pXL2319; the 0.5 kb NdeI-KpnI insert of pXL2325 at the NdeI and KpnI sites of pXL2319 in order to obtain pXL2320. (pXL2325 contains the first 500 bases of the gene where a CAT sequence has been introduced by mutagenesis, just upstream of the ATG initiation codon, in order to create an NdeI site). The grlB gene expression cassette contained in pXL2320 was cloned at the BglII and EcoRI sites of pKT230 (Bagdasarian et al., 1981) in order to obtain pXL2439. The expression plasmid pXL2340, see FIG. 2, containing the grlA gene in the vector pRSETB was constructed by cloning 1) the 1.7 kb NdeI-EcoRI insert of pXL2324 at the NdeI and EcoRI sites of the vector pRSETB in order to generate pXL2338; the 0.75 kb NdeI insert of pXL2337 at the NdeI sites of pXL2338 in order to obtain pXL2340. (pXL2337 contains the first 750 bases of the gene where a CATATG sequence has been introduced by mutagenesis, in place of the GTG initiation codon in order to create an NdeI site).

The plasmids pXL2320, or pXL2340 were introduced into the E. coli XL-1-Blue strain (Stratagen) and the expression of the genes was induced when the T7 phage RNA polymerase was produced after induction of the gene, encoding the T7 phage RNA polymerase, cloned into the helper phage M13/T7 (Studier et al., 1990, Invitrogen). The cellular extracts were analysed by electrophoresis on a PAGE-SDS gel stained with Coomasie blue as has already been described (Denèfle et al., 1987). In FIG. 3 is represented the production of a protein with a i) molecular weight of 79,000, when the grlB gene is induced in the E. coli strain XL1-blue, pXL2320; and ii) molecular weight of 90,000, when the grlA gene is induced in the E. coli strain XL1-Blue, pXL2340. The measured molecular weights are in agreement with the molecular weights deduced from the sequence.

3.3—Complementation of the parCts and parEts Mutants of Salmonella typhimurium by the grlA and grlB Genes of Staphylococcus aureus This example describes the heterologous complementation of the S. typhimurium parCts and parEts mutants by the S. aureus grlA and grlB genes. The plasmids pXL2320, pXL2340, pXL2439 or the vector pRSETB were introduced into the S. typhimurium strains SE7784 (parC281(Ts) zge-2393::Tn10 leu485) or SE8041 (parE206(Ts) zge-2393::Tn10 leu485) (Luttinger et al., 1991). No plasmid complements the heat-sensitive phenotype; on the other hand, when the plasmids pXL2340 and pXL2439 are introduced simultaneously into the SE7784 strain or into the SE8041 strain, the heat-sensitive phenotype of both strains is complemented. Consequently, the coexpression of the grlA and grlB genes of S. aureus allows the complementation of the ParC Ts or ParE Ts phenotype of the S. typhimurium mutants.

EXAMPLE 4

The DNA Topoisomerase IV of S. aureus is the Primary Target of the Fluoroquinolones This example describes the presence of a point mutation Ser-80 in the GrlA subunit with all the analysed clinical strains of S. aureus resistant to the fluoroquinolones whereas a mutation in the QRDR region (Quinolone Determining Region) (equivalent to the Ser-80 region of GrlA) in the GyrA subunit does not exist with the clinical strains of S. aureus weakly resistant to the fluoroquinolones. Consequently, the GrlA subunit is shown to be the primary target of the fluoroquinolones in S. aureus.

The genomic DNA of eight clinical strains of S. aureus and of a laboratory strain was prepared and used to amplify at 42° C. by PCR: i) the first 500 base pairs of gyrA using the sense oligonucleotide 5'-GGC GGATCCCATATGGCTGAATTACCTCA-3' (SEQ ID NO:13) and the antisense oligonucleotide 5'-GGC GGAAT TCGACGGCTCTCTTTCATTAC-3' (SEQ ID NO:14); ii) and the first 800 base pairs of grlA using the sense oligonucleotide 5'-GGCC GGATCCCATATGAGTGAAATAATTCAAGATT-3' (SEQ ID NO:15) and the antisense oligonucleotide -5'-GGCC GAATTCTAATAATTAACTGTTTACGTCC-3' (SEQ ID NO:16). Each amplified fragment was cloned into the phage M13mp18 and the sequence of the first 300 base pairs of each of the genes was read on 2 clones. The gyrA sequence is identical to that published by Magerrison and that of grlA to that described in SEQ ID No. 1, with the exception of the mutations presented in Table 4. The mutations in gyrA exist with the strains highly resistant to fluoroquinolones (SA4, SA5, SA6, SA35, SA42R and SA47; MIC for ciprofloxacin>16 mg/l); these mutations are a base change which leads to changes in the amino acids Ser-84 or Ser-85 or Glu-88. A mutation in grlA exists with all the strains resistant to fluoroquinolones and corresponds to the changing of the residue Ser-80 to Phe or Tyr.

TABLE 4

| Strain | MIC mg/l Ciprofloxacin | Mutation in gyrA | | Mutation in grlA | |
|---|---|---|---|---|---|
| | | Base | Codon | Base | Codon |
| RN4220* | 1 | no | no | no | no |
| SA42* | 0.5 | no | no | no | no |
| SAH** | 2 | no | no | 2281 G→A | $^{84}$Glu→Lys |
| SA1* | 2 | no | no | 2270 C→T | $^{80}$Ser→Phe |
| SAA** | 4 | no | no | 2281 G→A | $^{84}$Glu→Lys |
| SA3** | 4 | no | no | 2270 C→T | $^{80}$Ser→Phe |
| SA2** | 16 | no | no | 2270 C→A | $^{80}$Ser→Tyr |
| SA47* | 16 | 2533 C→T* | $^{84}$Ser→Leu | 2270 C→A | $^{80}$Ser→Tyr |
| SA4** | 32 | 2544 G→A | $^{88}$Glu→Lys | 2270 C→T | $^{80}$Ser→Phe |
| SA5** | 32 | 2533 C→T | $^{84}$Ser→Leu | 2270 C→T | $^{80}$Ser→Phe |
| SA6** | 32 | 2533 C→T | $^{84}$Ser→Leu | 2270 C→T | $^{80}$Ser→Phe |
| SA35* | 64 | 2535 T→C | $^{85}$Ser→Pro | 2270 C→A | $^{80}$Ser→Tyr |
| SA42R* | >128 | 2533 C→T* | $^{84}$Ser→Leu | 2270 C→A | $^{80}$Ser→Tyr |

*already published by Sreedharan et al. (1990)
**strains obtained from French state hospitals.

EXAMPLE 5

PCR (Polymerase chain Reaction) Amplification of the S. aureus DNA Fragment which is Inside grlA Containing a Point Mutation which Leads to a Substitution in GrlA from Ser-80 to Tyr (Ser-80→Tyr)

This example describes the production of the DNA fragment which is inside grlA of an S. aureus strain, SA2, resistant to fluoroquinolones. The grlA fragment contains a base change from C to A at position 2270 of the wild-type gene (FIG. 1). This mutation leads to a substitution of the residue Ser-80 to Tyr in the GrlA protein. It has been shown that a substitution of the residue Ser-80 to Phe or Tyr exists with all the strains weakly resistant to fluoroquinolones (Example 4). The fragment which is inside grlA was obtained after PCR amplification carried out at 50° C. with the genomic DNA of the SA2 strain and of the oligonucleotides 3358 and 3357 which correspond to position 2036 and 3435 respectively on the sequence of grlA. More specifically, the sense oligonucleotide 3358 (SEQ ID NO:15) (Example 4) and the antisense oligonucleotide 3357 made it possible to amplify a fragment of 1399 base pairs; the sequence of the antisense oligonucleotide 3357 is 5'-GGCCGAGCTCCAATTCTTCTTTTATGACATTC-3' (SEQ ID NO:17). The oligonucleotide 3358 was also used to introduce, by mutagenesis, a sequence CATATG, in place of the GTG initiation codon in order to create an NdeI site. The amplified grlA fragment was cloned into the BamHI/SstI cloning sites of pUC18 (Boehringer Mannheim), and 6 clones containing this plasmid, pXL2692, were analysed after sequencing their insert. In all cases, a sequence CATATG was introduced in place of the CTG initiation codon, and the point mutation at position 2270 of grlA (C→A) was again found.

EXAMPLE 6
Expression in *E. coli* of the grlA Gene Containing a Base Change Corresponding to the Change of the Residue Ser-80 to Tyr This example describes the construct prepared in order to express, in *E. coli*, the mutated grlA gene under the control of the T7 promoter (Studier et al., 1990). The expression plasmid pXL2742, containing the mutated grlA gene, was constructed by cloning the 0.75 kb insert of pXL2692 into the NdeI site of pXL2338 (Example 3.2). The plasmid pXL2742 was introduced into the *E. coli* XL1-Blue strain and the expression of the grlA gene was carried out as described in Example 3.2. The production of a protein having a molecular weight of 90,000 was obtained with the plasmid pXL2742 containing the grlA gene. The molecular weight measured is in agreement with the molecular weight deduced from the sequence of the grlA gene, and that already obtained for the wild-type GrlA protein (Example 3.2).

EXAMPLE 7
DNA Topoisomerase IV Activity of the GrlAB Protein of *S. aureus*

This example illustrates how an acellular extract containing the GrlAB protein can be prepared and how the enzymatic activity of the GrlAB protein present in this extract can be detected and measured.

7.1—Preparation of the Cell Extracts

An acellular extract of the *E. coli* strain XL1-blue pXL2340 expressing the GrlA protein is prepared for example in the following manner: The *E. coli* strain XL1-blue pXL2340 is cultured as follows: 250 ml of LB medium containing ampicillin at 50 mg/l are inoculated at 1/100 with a culture of *E. coli* XL1-blue pXL2340, and incubated at 30° C.; when the optical density at 600 nm is 0.3, 1 mM IPTG is added; after incubating for 30 min at 37° C., the strain is infected with the helper phage M13/T7 with a multiplicity of infection of 5 pfu per cell for 4 hours. After centrifugation (5000×g; 20 min), the cells obtained using 1.5 liters of culture are resuspended in 20 ml of 50 mM Tris/HCl buffer pH 7.8 containing 10 mM EDTA, 150 mM NaCl, 1 mM DTT, 0.12% Brij 58 and 0.75 mg/ml of lysozyme. After 30 min at 4° C., the mixture is centrifuged for 1 h at 50,000×g and the supernatant containing the GrlA protein is recovered. A change of buffer is carried out on this sample by chromatographing the extract through a column filled with Sephadex G625 (Pharmacia) equilibrated and eluted with the 50 mM Tris/HCl buffer pH 7.5 containing 1 mM EDTA, 5 mM DTT, 100 mM NaCl and 10% sucrose.

An acellular extract containing the GrlB protein is prepared in a similar manner using the *E. coli* strain XL1-blue pXL2320.

7.2—Purification of the DNA Topoisomerase IV of *S. aureus*

This example illustrates how an *S. aureus* enzyme catalysing the segregation of the daughter chromosomes during the final phase of replication (topoisomerase IV) can be purified.

The purification of the two GrlA and GrlB subunits of topoisomerase IV is carried out as described below, using the decatenation activity assay described in Example 7.3 to detect the presence of the GrlA and GrlB proteins during the purification, as is commonly used by persons skilled in the art. During the assay of this enzymatic activity, complementation of the fractions containing the GrlA protein is obtained with 1 μg of proteins of an extract of the *E. coli* strain XL1-blue pXL2320 expressing the GrlB subunit, and complementation of the fraction containing the GrlB protein is obtained with 1 μg of proteins of an extract of the *E. coli* strain XL1-blue pXL2340 expressing the GrlA subunit. A preferred mode of preparation of the enzymatic extracts is described in Example 7.1. Between each stage, the fractions containing the desired protein are frozen and stored at −70° C. The purification of the A subunit may be carried out by chromatography, for example, according to the following procedure:

an acellular extract prepared as described in Example 7.1 using about 5 g of cells of *E. coli* XL1-blue pXL2340 is chromatographed on a MonoQ HR 10/10 column (Pharmacia) at a flow rate of 3 ml/min with a linear gradient of NaCl (0.1M to 0.6M over 60 min) in a 10 mM Tris/HCl buffer pH 8.0 containing 1 mM EDTA, 1 mM DTT and 10% glycerol (w/v). The active fractions are combined and the sample is chromatographed on a Superdex 200 HiLoad 26/60 column (Pharmacia) equilibrated and eluted with 50 mM Tris/HCl buffer pH 7.5 containing 1 mM EDTA, 5 mM DTT and 0.25 M NaCl. The GrlA protein, which exists in the form of a symmetrical peak, is coeluted with the desired activity. After this stage, the preparation shows a single visible band in SDS-PAGE after developing with silver nitrate, and this band migrates with an apparent molecular weight of about 90,000.

The purification of the B subunit may be carried out by chromatography, for example, according to the following procedure: an acellular extract prepared as described in Example 5 using about 5 g of cells of *E. coli* XL1-blue pXL2320 is injected onto a Novobiocin-Sepharose CL-6B column (6 ml of gel prepared according to the procedure described by Staudenbauer et al., 1981, Nucleic Acids Research) equilibrated in 50 mM Tris/HCl buffer pH 7.5 containing 1 mM EDTA, 5 mM DTT and 0.3 M NaCl. After washing the column with the same buffer, the GrlB protein is eluted with 50 mM Tris/HCl buffer pH 7.5 containing 1 mM EDTA, 5 mM DTT and 2 M NaCl and 5 M urea. This fraction is then chromatographed on a Superdex 200 HiLoad 26/60 gel permeation column (Pharmacia) equilibrated and eluted with 50 mM Tris/HCl buffer pH 7.5 containing 1 mM EDTA, 5 mM DTT and 0.25 M NaCl. The GrlB protein, which exists in the form of a symmetrical peak, is coeluted with the desired activity. After this stage, the preparation has a single visible band in SDS-PAGE after developing with silver nitrate, and this band migrates with an apparent molecular weight of about 80,000.

7.3—Detection of the Enzymatic Activities of the GrlAB Protein

The various enzymatic activities of the GrlAB protein are detected by incubating, in the same reaction mixture, equal quantities of the two types of extracts prepared by the process described above or by any other process which makes it possible to recover the intracellular enzymatic proteins of the microorganism while preserving their activity, such as for example the procedures involving the use of presses (such as the French Press, the X-Press), or the use of ultrasound.

The ATP-dependent supercoiled DNA relaxing activity can be detected by carrying out the procedure, for example, in the following manner: a mixture of an extract of the *E. coli* strain XL1-blue pXL2320 (1 μg of proteins) and of an extract of the *E. coli* strain XL1-blue pXL2340 (1 μg of proteins) is incubated for 1 h at 37° C. in 30 μl of 50 mM Tris/HCl buffer pH 7.7 containing 4 mM ATP, 6 mM MgCl$_2$, 5 mM DTT, 1 mM spermidine, 20 mM KCl, 50 μg/ml of bovine serum albumin and 500 ng of supercoiled plasmid pBR322. The reaction is stopped by adding 7 μl of a 5% SDS and 2.5 mg/ml proteinase K mixture and the samples are incubated for a second period of 30 min at 37° C. and then analysed by electrophoresis on 1% agarose gel in 0.1M Tris/borate buffer pH 8.3 containing 2 mM EDTA at 6V/cm for 3 h. The separation of the relaxed and nicked (open circular) DNAs is carried out by performing an additional 2 h electrophoretic run after addition of ethidium bromide (1 μg/ml) to the running buffer. The DNA is then quantified by scanning the negatives of photographs of the gels (Polaroid type 665 film) with the aid of a Bioimage 50S apparatus (Millipore).

FIG. 4 shows that the acellular extracts of the strains *E. coli* XL1-blue pXL2320 and *E. coli* XL1-blue pXL2340 exhibit in a mixture an intense DNA relaxing activity whereas each of the extracts is inactive when it is incubated alone. The reaction is ATP-dependent. Furthermore, these two extracts, alone or in the form of a mixture, exhibit no DNA supercoiling activity, an activity typical of gyrase.

The ATP-dependent activity of decatenation of intertwined circular DNA molecules (catenanes) can be detected by carrying out the procedure, for example, in the following manner: a mixture of an extract of the *E. coli* strain XL1-blue pXL2320 (2.5 μg of proteins) and of an extract of the *E. coli* strain XL1-blue pXL2340 (2.5 μg of proteins) is incubated for 1 h at 37° C. in 40 μl of 50 mM Tris/HCl buffer pH 7.7 containing 1 mM ATP, 6 mM MgCl2, 200 mM glutamate, 10 mM DTT, 10 mM NaCl, 50 μg/ml of bovine serum albumin and 800 ng of kinetoplast DNA [consisting of a network of intertwined DNA molecules (catenanes) obtained from *Crithidia fasciculata*; TopoGene]. The reaction is stopped by adding 7 μl of a 250 mM EDTA solution (incubation 5 min at 37° C.), 5 μl of a 5% SDS and 2.5 mg/ml proteinase K mixture (incubation 30 min at 37° C.). The mixture is then analysed by electrophoresis on a 1% agarose gel in a 0.1M Tris/borate buffer pH 8.3 containing 2 mM EDTA at 6V/cm for 2 h 30 min. After staining the DNA with ethidium bromide (1 μg/ml), the DNA is quantified by scanning the negatives of photographs of the gels (Polaroid type 665 film) with the aid of a Bioimage 50S apparatus (Millipore). By working, for example, under the conditions described above, the extracts of the two strains *E. coli* XL1-blue pXL2320 and *E. coli* XL1-blue pXL2340 exhibit, in the form of a mixture, an activity of complete decatenation of the starting kinetoplast DNA. This activity is detected by the appearance of a DNA band with a size of about 2.5 kb and by the disappearance of the band of catenated DNA of very large size which penetrates very little into the gel during the electrophoretic run (FIG. 5). The *E. coli* gyrase introduced as a control into this assay exhibits no decatenation activity contrary to DNA topoisomerase IV of *E. coli* which completely decatenates the kinetoplast DNA (FIG. 5).

EXAMPLE 8
DNA Topoisomerase IV Activity of the GrlAB Protein of *S. aureus* whose GrlA Subunit Exhibits a Substitution of the Residue Ser-80 to Tyr (Ser-80→Tyr)

8.1—Preparation of a Cell Extract Containing the GrlAB Protein of *S. aureus* whose GrlA Subunit Exhibits a Substitution of the Residue Ser-80 to Tyr (Ser-80→Tyr)

This example illustrates how an acellular extract containing the protein GrlA$_{(Ser-80\rightarrow Tyr)}$B can be prepared, and how the enzymatic activity of the protein GrlA$_{(Ser-80\rightarrow Tyr)}$B can be detected and measured.

An acellular extract of the *E. coli* strain XL1-Blue pXL2742 expressing the protein GrlA$_{(Ser}$-80→Tyr)is prepared, for example, as described in Example 7 for the wild-type GrlA protein.

8.2—Purification of a DNA Topoisomerase IV of *S. aureus* Exhibiting an Ser-80-Tyr Mutation in the GrlA Subunit This example illustrates how a topoisomerase IV of *S. aureus* exhibiting an Ser-80→Tyr mutation in the GrlA subunit can be purified. The GrlA subunit of topoisomerase IV having an Ser-80→Tyr mutation is purified according to a procedure identical to that described in Example 7.2 using a culture of the *E. coli* strain XL1-blue pXL2742 constructed as described in Example 6.

8.3—Detection of the Enzymatic Activities

The ATP-dependent activities of supercoiled DNA relaxation, on the one hand, and of decatenation of intertwined circular DNA molecules, on the other hand, are detected in this extract as described in Example 7, by incubating, in the same reaction mixture, an acellular extract of the *E. coli* strain XL1-Blue pXL2742 containing the protein GrlA$_{(Ser-80\rightarrow Tyr)}$ and an extract of the *E. coli* strain XL1-Blue pXL2320 containing the GrlB protein.

EXAMPLE 9
Inhibition by Fluoroquinolones, of the DNA Topoisomerase IV Activity of the Wild-type GrlAB Protein of *S. aureus* and Resistance to Fluoroquinolones of the Protein Containing an Ser-80→Tyr transition in the GrlA Subunit The two methods described in Example 7 for the assay of DNA topoisomerase IV activities can be used to detect novel molecules which act as inhibitors of topoisomerase IV of *S. aureus* or to characterize the behaviour of topoisomerase IV of *S. aureus* towards molecules already identified as inhibitors of other topoisomerases (for example the fluoroquinolones).

In the test of relaxation of supercoiled DNA for example, the disappearance or the decrease in the relaxed DNA band during analysis of the reaction mixture after incubation of the GrlAB protein of *S. aureus* in the presence of a molecule or of a mixture of several molecules indicates that this molecule (or these molecules), inhibit the relaxation activity of GrlAB, and is therefore potentially antibacterial. However, since the studies carried out up until now (described in Example 7) have demonstrated that the GrlAB protein is a topoisomerase IV, and since it is nowadays established that the major function of the topoisomerases IV is decatenation (or disentanglement) of the intertwined daughter chromosomes during the final stages of replication, it seems more judicious to search for the inhibitors of the GrlAB protein using a test of decatenation of DNA using, for example, the test described in Example 7.3. To carry out the experiments described in the examples which follow, the incubations are carried out with the purified wild-type GrlAB proteins as described in Example 7, and with the mutant protein GrlA$_{(Ser-80\rightarrow Tyr)}$B as described in Example 8. The two wild-type and mutant GrlAB proteins are reconstituted by mixing equimolar quantities of their two GrlA and GrlB subunits. In the decatenation test, if the disappearance or the decrease in the intensity of the decatenated DNA band is observed during analysis of the reaction mixture after incubation of the GrlAB protein in the presence of a molecule or of a mixture of several molecules, this indicates that this molecule (or these molecules) inhibits the decatenation activity of the GrlAB protein, and is therefore potentially antibacterial. Since it has been demonstrated in the present invention that the GrlAB protein is the primary target for the molecules of the fluoroquinolone family, it appears that the fluoroquinolones must act as inhibitors in the decatenation test described in Example 7. Indeed, when the purified GrlAB protein is incubated in the presence of increasing quantities of a fluoroquinolone, for example ciprofloxacin, it appears that above a concentration of 10 μg/ml, ciprofloxacin completely inhibits the activity of decatenation of the kinetoplast DNA. Ciprofloxacin inhibits 50% of the activity of decatenation of kinetoplast DNA at a concentration of 4.0 µg/ml. Likewise, sparfloxacin which is another fluoroquinolone inhibits 50% of the activity of decatenation of kinetoplast DNA at a concentration of 6.0 µg/ml. Likewise, since it has been demonstrated in the present invention (Example 4) that the presence of an Ser-80→Tyr mutation on the GrlA subunit of the mutant GrlAB protein confers on the strain a certain level of resistance to fluoroquinolones, for example ciprofloxacin, it appears that the fluoroquinolones must act on this mutant DNA topoisomerase IV as inhibitors which are less efficient in the decatenation test described in Example 7. Indeed, when the mutant protein GrlA$_{(Ser-80 \to Tyr)}$B is incubated in the presence of increasing quantities of a fluoroquinolone, for example ciprofloxacin, it appears that ciprofloxacin inhibits 50% of the activity of decatenation of kinetoplast DNA at a concentration of 60 µg/ml, that is to say a concentration 15 times as high as that necessary to obtain the same effect with the wild-type enzyme. Likewise, in the presence of the mutant enzyme GrlA$_{(Ser-80 \to Tyr)}$B, sparfloxacin inhibits 50% of the activity of decatenation of kinetoplast DNA at a concentration of 500 µg/ml, that is to say a concentration 80 times as high as that necessary to obtain the same effect with the wild-type enzyme. Norfloxacin inhibits 50% of the activity of decatenation of kinetoplast DNA at a concentration of 12 µg/ml with the wild-type GrlAB enzyme and exhibits the same inhibitory activity at a concentration of 125 µg/ml with the enzyme GrlA$_{(Ser-80 \to Tyr)}$B. Ofloxacin inhibits 50% of the activity of decatenation of kinetoplast DNA at a concentration of 10 µg/ml with the wild-type GrlAB enzyme and has the same inhibitory activity at a concentration of 250 µg/ml with the enzyme GrlA$_{(Ser-80 \to Tyr)}$B.

Novobiocin, whose mechanism of action is different from that of the fluoroquinolones, should therefore in principle have the same inhibitory activity on both the wild-type GrlAB enzyme and on the mutant GrlA$_{(Ser-80 \to Tyr)}$B enzyme in the decatenation test described in Example 7. Indeed, novobiocin inhibits 50% of the activity of decatenation of kinetoplast DNA at a concentration of about 30 µg/ml whatever the enzyme used (wild-type GrlAB or mutant GrlA$_{(Ser-80 \to Tyr)}$).

ABBREVIATIONS

DNA: deoxyribonucleic acid
RNA: ribonucleic acid
MIC: minimum inhibitory concentration
IPTG: isopropylthio-β-D-galactoside
LB: Luria-Bertani medium
PAGE: electrophoresis gel containing acrylamide and N,N'-methylenebisacrylamide
PCR: polymerase chain reaction
pfu: plaque forming unit
QRDR: region of the GyrA subunit where the point mutations leading to resistance to fluoroquinolones are mapped
SDS: sodium dodecyl sulphate
Tris: tris(hydroxymethyl)aminomethane

REFERENCES

Adachi, T., Mizuuchi, M., Robinson, E. A., Apella, E., O'Dea, M. H., Gellert, M., and Mizuuchi K. (1987) DNA sequence of the *E. coli* gyrB gene: application of a new sequencing strategy. *Nucl Acid Res* 15: 771–784.
Bagdasarian, M., Lurz, R., Rückert, B., Franklin, F. C., Bagdasarian, M. M., Frey, J., and Timmis, K. (1981) Specific-purpose plasmid cloning vectors. II. Broad host range, high copy number, RSF1010-derived vectors, and a host-vector system for gene cloning in Pseudomonas. *Gene* 16: 237–247.
Colman, S. D., Hu, P. C., and Bott, K. F. (1990) *Mycoplasma pneumoniae* DNA gyrase genes. *Mol Microbiol* 4: 1129–11134.
Cullen, M. E., Wyke, A. W., Kuroda, R., and Fisher, L. M. (1989) Cloning and characterization of a DNA gyrase gene from *Escherichia coli* that confers clinical resistance to 4-quinolones *Antimicrob Agents Chemother* 33: 886–894.
Denefle, P., Kovarik, S., Guiton, J. D., Cartwright, T., and Mayaux, J.-F. (1987) Chemical synthesis of a gene coding for human angiogenin, its expression in *Escherichia coli* and conversion of the product into its active form. *Gene* 56: 61–70.
Gellert, M., Mizuuchi, K., O'Dea, M. H. and Nash, H. A. (1976) DNA gyrase: an enzyme that introduces superhelical turns into DNA *Proc Natl Acad Sci USA* 73: 3872–3876.
Goswitz, J. J., Willard, K. E., Fasching, C. E., and Peterson, L. R. (1992) Detection of gyrA gene mutations associated with ciprofloxacin resistance in methicillin-resistant *Staphylococcus aureus*: analysis by polymerase chain reaction and automated direct DNA sequencing. *Antimicrob Agents Chemother* 36: 1166–1169.
Higgins, D. G., and Sharp, P. M. (1988) Clustal: a package for performing multiple sequence alignment on a microcomputer. *Gene* 73: 237–244.
Holmes, M. L., and Dyall-Smith, M. (1991) Mutations in the DNA gyrase result in novobiocin resistance in halophilic archaebacteria. *J Bacteriol* 173: 642–648.
Hooper, D. C., Wolfson, J. S. (1993) Mechanisms of quinolone action and bacterial killing. In Quinolone Antimicrobial Agents. Hooper, D. C., Wolfson, J. S. (eds) Washington: American Society of Microbiology, pp. 53–75.
Horowitz, D. S., and Wang, J. C. (1987) Mapping of the active site tyrosine of *Escherichia coli* DNA gyrase. *J Biol Chem* 262: 5339–5344.
Huang, W. M. (1992) Multiple DNA gyrase-like genes in Eubacteria. In *Molecular Biology of DNA Topoisomerases and its Application to Chemotherapy*. Andoh, T., Ikeda, H., and Oguro, M. (eds). London: CRC Press, pp. 39–48.
Kanehisa, M. (1984) Use of statistical criteria for screening potential homologies in nucleic acids sequences. *Nucl Acids Res* 12: 203–215.
Kato, J., Suzuki, H., and Ikeda, H. (1992) Purification and characterization of DNA topoisomerase-IV in *Escherichia coli*. J Biol Chem 267: 25676–25684.
Kato, J., Nishimura, Y., Imamura, R., Niki, H., Higara, S., and Suzuki, H. (1990) New topoisomerase essential for chromosome segregation in *E. coli. Cell* 63: 393–404.
Luttinger, A. L., Springer, A. L., and Schmid, M. B. (1991) A cluster of genes that affects nucleoid segregation in *Salmonella typhimurium*. *New Biol* 3: 687–697.
Margerrison, E. E. C., Hopewell, R. and L. M. Fisher. (1992) Nucleotide sequence of the *Staphylococcus aureus* gyrB-gyrA locus encoding the DNA gyrase A and B proteins. *J Bacteriol* 174: 1596–1603.
Maxwell, A. (1992) The molecular basis of quinolone action. *J. Antimicrob. Chemother.* 330: 409–416.
Moriya, S., Ogasawara, N. and Yoshida, H. (1985) Structure and function of the region of the replication origin of *Bacillus subtilis* chromosome. III. Nucleotide sequence of some 10,000 base pairs in the origin region. *Nucl Acid Res* 13: 2251–2265.
Normark, S., Bergtröm, S., Edlund, T., Grundström, T., Jaurin, B., Lindberg, F., and Olsson, O. (1983) Overlapping genes. *Ann Rev Genet* 17: 499–525.

Novick, R. P. (1990) The staphylococcus as a molecular genetic system. In *Molecular Biology of the Staphylococci*. Novick, R. P. (ed). New York: VCH Publishers, pp. 1–37.

Parales, R. E., and Harwood, C. S. (1990) Nucleotide sequence of the gyrB gene of *Pseudomonas putida*. *Nucl Acid Res* 18: 5880–5880.

Peng, H., Marians, K. J. (1993 (a)) *Escherichia coli* topoisomerase IV Purification, characterization, subunit structure, and subunit interactions. *J Biol Chem* 268: 24481–24490.

Peng, H., Marians, K. J. (1993 (b)) Decatenation activity of topoisomerase IV during oriC and pBR322 DNA replication in vitro. *Proc Natl Acad Sci USA* 90: 8571–8575.

Sambrook J., Fritsch, E. F., and Maniatis, T. (1989) Molecular Cloning: a Laboratory Manual 2nd edn. Cold Spring Harbor, N.Y.: Cold Spring Harbor Laboratory Press.

Sreedharan, S., Peterson, L., and Fisher, L. M. (1991) Ciprofloxacin-resistance in coagulase-positive and -negative Staphylococci: role of mutations at serine 84 in the DNA gyrase A protein of *Staphylococcus aureus*: and *Staphylococcus epidermidis Antimicrob Agents Chemother* 35: 2151–2154.

Sreedharan, S., Oram, M., Jensen, B., Peterson, L., and Fisher, L. M. (1990) DNA gyrase gyrA mutations in ciprofloxacin-resistant strains of *Staphylococcus aureus*: close similarity with quinolone resistance mutations in *Escherichia coli*. *J Bacteriol* 172: 7260–7262.

Staden, R., and McLachlan, A. D. (1982) Codon preference and its use in identifying protein coding regions in long DNA sequences. *Nucl Acid Res* 10: 141–156.

Staudenbauer, W. L., and Orr, E. (1981) DNA gyrase: affinity chromatography on novobiocin-Sepharose and catalytic properties *Nucleic Acid Research* 9: 3589–3603.

Stein, D. C., Danaher, R. J., and Cook, T. M. (1991) Characterization of a gyrB mutation responsible for low-level nalidixic acid resistance in *Neisseria gonorrhoeae*. *Antimicrob Agents Chemother* 35: 622–626.

Studier, W. F., Rosenberg, A. H., Dunn, J. J., and Duberndorff, J. W. (1990) Use of T7 RNA polymerase to direct expression of cloned genes. *Methods Enzymol.* 185: 89–60.

Swamberg, S. L. and Wang, J. C. (1987) Cloning and sequencing of the *Escherichia coli* DAN gyrA gene coding for the A subunit of DNA gyrase. *J Mol Biol* 197: 729–736.

Thiara, A. M., and Cundliffe, E. (1993) Expression and analysis of two gyrB genes from the novobiocin producer, *Streptomyces sphaeroides*. *Mol Microbiol* 8: 495–506.

Wang, J. C., and Liu, L. F. (1990) DNA replication: topological aspect and the roles of DNA topoisomerases. In *DNA Topology and its Biological Effects*. Cozzarelli, N. R., and Wang, J. C. (eds). New York: Cold Spring Harbor Laboratory Press, pp. 321–340.

Wang, Y., Huang, W. M. and Taylor, D. E. (1993) Cloning and nucleotide sequence of the *Campylobacter jejuni* gyrA gene and characterization of quinolone resistance mutations. *Antimicrob Agents and Chemother* 37: 457–463.

Wigley, D. B., Davies, G. J., Dodson, E. J., Maxwell, A., and Dodson, G. (1991) Crystal structure of an $NH_2$-terminal fragment of the DNA gyrase B protein. *Nature* 351: 624–629.

Yoshida, H., Bogaki, M., Nakamura, M., and Nakamura, S. (1990) Quinolone resistance determining region in the DNA gyrase gene of *Escherichia coli*. *Antimicrob Agents Chemother* 34: 1271–1272.

We claim:

1. An isolated nucleotide sequence encoding a subunit of topoisomerase IV of *Staphylococcus aureus*.

2. An isolated nucleotide sequence which encodes a subunit of topoisomerase IV chosen from:

(a) all or part of the grlA gene (SEQ ID NO: 4) or grlB gene (SEQ ID NO: 6), (b) a sequence which hybridizes with the sequence of SEQ ID NO:4 or SEQ ID NO:6 and encodes a subunit of a topoisomerase IV, and (c) a sequence derived from the sequences of (a) and (b) because of the degeneracy of the genetic code.

3. Nucleotide sequence according to claim 1, characterized in that it is the grlA gene (SEQ ID NO:4).

4. Nucleotide sequence according to claim 1, characterized in that it is the grlB gene (SEQ ID NO:6).

5. Nucleotide sequence according to claim 1, characterized in that it is the grlA gene having a mutation resulting in a resistance towards molecules of the quinolone family.

6. Nucleotide sequence according to claim 5, characterized in that it is the grlA gene having a base A as a substitution for a base C at position 2270 of SEQ ID NO:4.

7. Recombinant DNA comprising a nucleotide sequence according to claim 1.

8. Autonomously replicating and/or integrative expression vector characterized in that it comprises a nucleotide sequence according to claim 1.

9. Recombinant cell containing a nucleotide sequence encoding a subunit of topoisomerase IV of *Staphylococcus aureus* and/or an autonomously replicating and/or integrative expression vector according to claim 8.

10. Cell according to claim 9, characterized in that it is a bacterium.

11. Process for the production of a polypeptide, characterized in that the polypeptide is expressed from a recombinant cell containing a nucleotide sequence chosen from:
    (a) the grlA (SEQ ID NO:4) or grlB (SEQ ID NO:6) genes,
    (b) the sequences hybridizing with all or part of the (a) genes and encoding a subunit of a topoisomerase IV, and
    (c) the sequence derived from the (a) and (b) sequences because of degeneracy of the genetic code, and/or an autonomously replicating and/or integrative expression vector according to claim 8, is cultured and the polypeptide produced is recovered.

12. Nucleotide sequence according to claim 2, characterized in that it is the grlA gene (SEQ ID NO:4).

13. Nucleotide sequence according to claim 2, characterized in that it is the grlB gene (SEQ ID NO:6).

14. Nucleotide sequence according to claim 2, characterized in that it is the grlA gene having a mutation resulting in a resistance towards molecules of the quinolone family.

15. Recombinant DNA comprising a nucleotide sequence according to claim 2.

16. Autonomously replicating and/or integrative expression vector characterized in that it comprises a nucleotide sequence according to claim 2.

17. A process for the production of a polypeptide comprising the polypeptide GrlA (SEQ ID NO:3), or the polypeptide GrlB (SEQ ID NO:5), or a derivative thereof obtained by substitution or deletion of one or more residues while still retaining the topoisomerase activity of said GrlA (SEQ ID No.: 3) or GrlB (SEQ ID No.: 5), characterized in that a recombinant cell is cultured and said polypeptide is recovered.

\* \* \* \* \*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 4565 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAATTCCGAC GTACGTTTGC AGGAGGCGAA ATCATTGGCA ATGAATAAAC AAAATAATTA      60

TTCAGATGAT TCAATACAGG TTTTAGAGGG GTTAGAAGCA GTTCGTAAAA GACCTGGTAT     120

GTATATTGGA TCAACTGATA AACGGGGATT ACATCATCTA GTATATGAAA TTGTCGATAA     180

CTCCGTCGAT GAAGTATTGA ATGGTTACGG TAACGAAATA GATGTAACAA TTAATAAAGA     240

TGGTAGTATT TCTATAGAAG ATAATGGACG TGGTATGCCA ACAGGTATAC ATAAATCAGG     300

TAAACCGACA GTCGAAGTTA TCTTTACTGT TTTACATGCA GGAGGTAAAT TTGGACAAGG     360

TGGCTATAAA ACTTCAGGTG GTCTTCACGG CGTTGGTGCT TCAGTGGTAA ATGCATTGAG     420

TGAATGGCTT GAAGTTGAAA TCCATCGAGA TGGTAATATA TATCATCAAA GTTTTAAAAA     480

CGGTGGTTCG CCATCTTCAG GTTTAGTGAA AAAAGGTAAA ACTAAGAAAA CAGGTACCAA     540
```

```
AGTAACATTT AAACCTGATG ACACAATTTT TAAAGCATCT ACATCATTTA ATTTTGATGT    600

TTTAAGTGAA CGACTACAAG AGTCTGCGTT CTTATTGAAA AATTTAAAAA TAACGCTTAA    660

TGATTTACGC AGTGGTAAAG AGCGTCAAGA GCATTACCAT TATGAAGAAG GAATCAAAGA    720

GTTTGTTAGT TATGTCAATG AAGGAAAAGA AGTTTTGCAT GACGTGGCTA CATTTTCAGG    780

TGAAGCAAAT GGTATAGAGG TAGACGTAGC TTTCCAATAT AATGATCAAT ATTCAGAAAG    840

TATTTTAAGT TTTGTAAATA ATGTACGTAC TAAAGATGGT GGTACACATG AAGTTGGTTT    900

TAAAACAGCA ATGACACGCG TATTTAATGA TTATGCACGT CGTATTAATG AACTTAAAAC    960

AAAAGATAAA AACTTAGATG GTAATGATAT TCGTGAAGGT TTAACAGCTG TTGTGTCTGT   1020

TCGTATTCCA GAAGAATTAT TGCAATTTGA AGGACAAACG AAATCTAAAT TGGGTACTTC   1080

TGAAGCTAGA AGTGCTGTTG ATTCAGTTGT TGCAGACAAA TTGCCATTCT ATTTAGAAGA   1140

AAAAGGACAA TTGTCTAAAT CACTTGTGAA AAAAGCGATT AAAGCACAAC AAGCAAGGGA   1200

AGCTGCACGT AAAGCTCGTG AAGATGCTCG TTCAGGTAAG AAAAACAAGC GTAAAGACAC   1260

TTTGCTATCT GGTAAATTAA CACCTGCACA AGTAAAAAAC ACTGAAAAAA ATGAATTGTA   1320

TTTAGTCGAA GGTGATTCTG CGGGAGGTTC AGCAAAACTT GGACGAGACC GCAAATTCCA   1380

AGCGATATTA CCATTACGTG GTAAGGTAAT TAATACAGAG AAAGCACGTC TAGAAGATAT   1440

TTTTAAAAAT GAAGAAATTA ATACAATTAT CCACACAATC GGGGCAGGCG TTGGTACTGA   1500

CTTTAAAATT GAAGATAGTA ATTATAATCG TGTAATTATT ATGACTGATG CTGATACTGA   1560

TGGTGCGCAT ATTCAAGTGC TATTGTTAAC ATTCTTCTTC AAATATATGA AACCGCTTGT   1620

TCAAGCAGGT CGTGTATTTA TTGCTTTACC TCCACTTTAT AAATTGGAAA AAGGTAAAGG   1680

CAAAACAAAG CGAGTTGAAT ACGCTTGGAC AGACGAAGAG CTTAATAAAT TGCAAAAGA    1740

ACTTGGTAAA GGCTTCACGT TACAACGTTA CAAAGGTTTG GGTGAAATGA ACCCTGAACA   1800

ATTATGGGAA ACGACGATGA ACCCAGAAAC ACGAACTTTA ATTCGTGTAC AAGTTGAAGA   1860

TGAAGTGCGT TCATCTAAAC GTGTAACAAC ATTAATGGGT GACAAAGTAC AACCTAGACG   1920

TGAATGGATT GAAAAGCATG TTGAGTTTGG TATGCAAGAG GACCAAAGTA TTTTAGATAA   1980

TTCTGAAGTA CAAGTGCTTG AAAATGATCA ATTTGATGAG GAGGAAATCT AGTGAGTGAA   2040

ATAATTCAAG ATTTATCACT TGAAGATGTT TTAGGTGATC GCTTTGGAAG ATATAGTAAA   2100

TATATTATTC AAGAGCGTGC ATTGCCAGAT GTTCGTGATG GTTTAAAACC AGTACAACGT   2160

CGTATTTTAT ACGCAATGTA TTCAAGTGGT AATACACACG ATAAAAATTT CCGTAAAAGT   2220

GCGAAAACAG TCGGTGATGT TATTGGTCAA TATCATCCAC ATGGAGACTC CTCAGTGTAC   2280

GAAGCAATGG TCCGTTTAAG TCAAGACTGG AAGTTACGAC ATGTCTTAAT AGAAATGCAT   2340

GGTAATAATG GTAGTATCGA TAATGATCCG CCAGCGGCAA TGCGTTACAC TGAAGCTAAG   2400

TTAAGCTTAC TAGCTGAAGA GTTATTACGT GATATTAATA AAGAGACAGT TTCTTTCATT   2460

CCAAACTATG ATGATACGAC ACTCGAACCA ATGGTATTGC CATCAAGATT TCCTAACTTA   2520

CTAGTGAATG GTTCTACAGG TATATCTGCA GGTTACGCGA CAGATATACC ACCACATAAT   2580

TTAGCTGAAG TGATTCAAGC AACACTTAAA TATATTGATA ATCCGGATAT TACAGTCAAT   2640

CAATTAATGA AATATATTAA AGGTCCTGAT TTTCCAACTG GTGGTATTAT TCAAGGTATT   2700

GATGGTATTA AAAAAGCTTA TGAATCAGGT AAAGGTAGAA TTATAGTTCG TTCTAAAGTT   2760

GAAGAAGAAA CTTACGCAA TGGACGTAAA CAGTTAATTA TTACTGAAAT TCCATATGAA    2820

GTGAACAAAG GTAGCTTAGT AAAACGTATC GATGAATTAC GTGCTGACAA AAAAGTCGAT   2880

GGTATCGTTG AAGTACGTGA TGAAACTGAT AGAACTGGTT TACGAATAGC AATTGAATTG   2940
```

| | |
|---|---|
| AAAAAAGATG TGAACAGTGA ATCAATCAAA AATTATCTTT ATAAAAACTC TGATTTACAG | 3000 |
| ATTTCATATA ATTTCAACAT GGTCGCTATT AGTGATGGTC GTCCAAAATT GATGGGTATT | 3060 |
| CGTCAAATTA TAGATAGTTA TTTGAATCAT CAAATTGAGG TTGTTGCAAA TAGAACGAAG | 3120 |
| TTTGAATTAG ATAATGCTGA AAAACGTATG CATATCGTTG AAGGTTTGAT TAAAGCGTTG | 3180 |
| TCAATTTTAG ATAAAGTAAT CGAATTGATT CGTAGCTCTA AAAACAAGCG TGACGCTAAA | 3240 |
| GAAAACCTTA TCGAAGTATA CGAGTTCACA GAAGAACAGG CTGAAGCAAT TGTAATGTTA | 3300 |
| CAGTTATATC GTTAACAAA CACTGACATA GTTGCGCTTG AAGGTGAACA TAAAGAACTT | 3360 |
| GAAGCATTAA TCAAACAATT ACGTCATATT CTTGATAACC ATGATGCATT ATTGAATGTC | 3420 |
| ATAAAGAAG AATTGAATGA AATTAAAAAG AAATTCAAAT CTGAACGACT GTCTTTAATT | 3480 |
| GAAGCAGAAA TTGAAGAAAT TAAAATTGAC AAAGAAGTTA TGGTGCCTAG TGAAGAAGTT | 3540 |
| ATTTTAAGTA TGACACGTCA TGGATATATT AAACGTACTT CTATTCGTAG CTTTAATGCT | 3600 |
| AGCGGTGTTG AAGATATTGG TTTAAAAGAT GGTGACAGTT TACTTAAACA TCAAGAAGTA | 3660 |
| AATACGCAAG ATACCGTACT AGTATTTACA AATAAAGGTC GTTATCTATT TATACCAGTT | 3720 |
| CATAAATTAC GAGATATTCG TTGGAAAGAA TTGGGGCAAC ATGTATCACA AATAGTTCCT | 3780 |
| ATCGAAGAAG ATGAAGTGGT TATTAATGTC TATAATGAAA AGGACTTTAA TACTGATGCA | 3840 |
| TTTTATGTTT TTGCGACTCA AAATGGCATG ATTAAGAAAA GTACAGTGCC TCTATTTAAA | 3900 |
| ACAACGCGTT TTAATAAACC TTTAATTGCA ACTAAAGTTA AAGAAAATGA TGATTTGATT | 3960 |
| AGTGTTATGC GCTTTGAAAA AGATCAATTA ATTACCGTAA TTACAAATAA AGGTATGTCA | 4020 |
| TTAACGTATA ATACAAGTGA ACTATCAGAT ACTGGATTAA GGGCGGCTGG TGTTAAATCA | 4080 |
| ATAAATCTTA AAGTTGAAGA TTTCGTTGTT ATGACAGAAG GTGTTTCTGA AAATGATACT | 4140 |
| ATATTGATGG CCACACAACG CGGCTCGTTA AAACGTATTA GTTTTAAAAT CTTACAAGTT | 4200 |
| GCTAAAAGAG CACAACGTGG AATAACTTTA TTAAAAGAAT TAAAGAAAAA TCCACATCGT | 4260 |
| ATAGTAGCTG CACATGTAGT GACAGGTGAA CATAGTCAAT ATACATTATA TTCAAAATCA | 4320 |
| AACGAAGAAC ATGGTTTAAT TAATGATATT CATAAATCTG AACAATATAC AAATGGCTCA | 4380 |
| TTCATTGTAG ATACAGATGA TTTTGGTGAA GTAATAGACA TGTATATTAG CTAAAAACTA | 4440 |
| TATGCAATCA CGAAATTAAA TGATAAAATA CAGTAATGTT AAATTTTGAC TAAATTCAAG | 4500 |
| GGATTTATAT TAAATGCTGA CCAAGTACTT ATCGTTAAAT TAGCGATACG GAATCCGCGG | 4560 |
| AATTC | 4565 |

(2) INFORMATION FOR SEQ ID NO:2:

(i) SEQUENCE CHARACTERISTICS:
        (A) LENGTH: 4565 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| CTTAAGGCTG CATGCAAACG TCCTCCGCTT TAGTAACCGT TACTTATTTG TTTTATTAAT | 60 |
| AAGTCTACTA AGTTATGTCC AAAATCTCCC CAATCTTCGT CAAGCATTTT CTGGACCATA | 120 |
| CATATAACCT AGTTGACTAT TTGCCCCTAA TGTAGTAGAT CATATACTTT AACAGCTATT | 180 |
| GAGGCAGCTA CTTCATAACT TACCAATGCC ATTGCTTTAT CTACATTGTT AATTATTTCT | 240 |
| ACCATCATAA AGATATCTTC TATTACCTGC ACCATACGGT TGTCCATATG TATTTAGTCC | 300 |

```
ATTTGGCTGT CAGCTTCAAT AGAAATGACA AAATGTACGT CCTCCATTTA AACCTGTTCC    360

ACCGATATTT TGAAGTCCAC CAGAAGTGCC GCAACCACGA AGTCACCATT TACGTAACTC    420

ACTTACCGAA CTTCAACTTT AGGTAGCTCT ACCATTATAT ATAGTAGTTT CAAAATTTTT    480

GCCACCAAGC GGTAGAAGTC CAAATCACTT TTTTCCATTT TGATTCTTTT GTCCATGGTT    540

TCATTGTAAA TTTGGACTAC TGTGTTAAAA ATTTCGTAGA TGTAGTAAAT TAAAACTACA    600

AAATTCACTT GCTGATGTTC TCAGACGCAA GAATAACTTT TTAAATTTTT ATTGCGAATT    660

ACTAAATGCG TCACCATTTC TCGCAGTTCT CGTAATGGTA ATACTTCTTC CTTAGTTTCT    720

CAAACAATCA ATACAGTTAC TTCCTTTTCT TCAAAACGTA CTGCACCGAT GTAAAAGTCC    780

ACTTCGTTTA CCATATCTCC ATCTGCATCG AAAGGTTATA TTACTAGTTA TAAGTCTTTC    840

ATAAAATTCA AAACATTTAT TACATGCATG ATTTCTACCA CCATGTGTAC TTCAACCAAA    900

ATTTTGTCGT TACTGTGCGC ATAAATTACT AATACGTGCA GCATAATTAC TTGAATTTTG    960

TTTTCTATTT TTGAATCTAC CATTACTATA AGCACTTCCA AATTGTCGAC AACACAGACA   1020

AGCATAAGGT CTTCTTAATA ACGTTAAACT TCCTGTTTGC TTTAGATTTA ACCCATGAAG   1080

ACTTCGATCT TCACGACAAC TAAGTCAACA ACGTCTGTTT AACGGTAAGA TAAATCTTCT   1140

TTTTCCTGTT AACAGATTTA GTGAACACTT TTTTCGCTAA TTTCGTGTTG TTCGTTCCCT   1200

TCGACGTGCA TTTCGAGCAC TTCTACGAGC AAGTCCATTC TTTTTGTTCG CATTTCTGTG   1260

AAACGATAGA CCATTTAATT GTGGACGTGT TTCATTTTTG TGACTTTTTT TACTTAACAT   1320

AAATCAGCTT CCACTAAGAC GCCCTCCAAG TCGTTTTGAA CCTGCTCTGG CGTTTAAGGT   1380

TCGCTATAAT GGTAATGCAC CATTCCATTA ATTATGTCTC TTTCGTGCAG ATCTTCTATA   1440

AAAATTTTTA CTTCTTTAAT TATGTTAATA GGTGTGTTAG CCCCGTCCGC AACCATGACT   1500

GAAATTTTAA CTTCTATCAT TAATATTAGC ACATTAATAA TACTGACTAC GACTATGACT   1560

ACCACGCGTA TAAGTTCACG ATAACAATTG TAAGAAGAAG TTTATATACT TTGGCGAACA   1620

AGTTCGTCCA GCACATAAAT AACGAAATGG AGGTGAAATA TTTAACCTTT TTCCATTTCC   1680

GTTTTGTTTC GCTCAACTTA TGCGAACCTG TCTGCTTCTC GAATTATTTA ACGTTTTTCT   1740

TGAACCATTT CCGAAGTGCA ATGTTGCAAT GTTTCCAAAC CCACTTTACT TGGGACTTGT   1800

TAATACCCTT TGCTGCTACT TGGGTCTTTG TGCTTGAAAT TAAGCACATG TTCAACTTCT   1860

ACTTCACGCA AGTAGATTTG CACATTGTTG TAATTACCCA CTGTTTCATG TTGGATCTGC   1920

ACTTACCTAA CTTTTCGTAC AACTCAAACC ATACGTTCTC CTGGTTTCAT AAAATCTATT   1980

AAGACTTCAT GTTCACGAAC TTTTACTAGT TAAACTACTC CTCCTTTAGA TCACTCACTT   2040

TATTAAGTTC TAAATAGTGA ACTTCTACAA AATCCACTAG CGAAACCTTC TATATCATTT   2100

ATATAATAAG TTCTCGCACG TAACGGTCTA CAAGCACTAC CAAATTTTGG TCATGTTGCA   2160

GCATAAAATA TGCGTTACAT AAGTTCCACCA TTATGTGTGC TATTTTTAAA GGCATTTTCA   2220

CGCTTTTGTC AGCCACTACA ATAACCAGTT ATAGTAGGTG TACCTCTGAG GAGTCACATG   2280

CTTCGTTACC AGGCAAATTC AGTTCTGACC TTCAATGCTG TACAGAATTA TCTTTACGTA   2340

CCATTATTAC CATCATAGCT ATTACTAGGC GGTCGCCGTT ACGCAATGTG ACTTCGATTC   2400

AATTCGAATG ATCGACTTCT CAATAATGCA CTATAATTAT TTCTCTGTCA AGAAAGTAA   2460

GGTTTGATAC TACTATGCTG TGAGCTTGGT TACCATAACG GTAGTTCTAA AGGATTGAAT   2520

GATCACTTAC CAAGATGTCC ATATAGACGT CCAATGCGCT GTCTATATGG TGGTGTATTA   2580

AATCGACTTC ACTAAGTTCG TTGTGAATTT ATATAACTAT TAGGCATATA ATGTCAGTTA   2640

GTTAATTACT TTATATAATT TCCAGGACTA AAAGGTTGAC CACCATAATA AGTTCCATAA   2700
```

-continued

```
CTACCATAAT TTTTTCGAAT ACTTAGTCCA TTTCCATCTT AATATCAAGC AAGATTTCAA    2760

CTTCTTCTTT GAAATGCGTT ACCTGCATTT GTCAATTAAT AATGACTTTA AGGTATACTT    2820

CACTTGTTTC CATCGAATCA TTTTGCATAG CTACTTAATG CACGACTGTT TTTTCAGCTA    2880

CCATAGCAAC TTCATGCACT ACTTTGACTA TCTTGACCAA ATGCTTATCG TTAACTTAAC    2940

TTTTTTCTAC ACTGTCACT  TAGTTAGTTT TTAATAGAAA TATTTTTGAG ACTAAATGTC    3000

TAAAGTATAT TAAAGTTGTA CCAGCGATAA TCACTACCAG CAGGTTTTAA CTACCCATAA    3060

GCAGTTTAAT ATCTATCAAT AAACTTAGTA GTTTAACTCC AACAACGTTT ATCTTGCTTC    3120

AAACTTAATC TATTACGACT TTTTGCATAC GTATAGCAAC TTCCAAACTA ATTTCGCAAC    3180

AGTTAAAATC TATTTCATTA GCTTAACTAA GCATCGAGAT TTTTGTTCGC ACTGCGATTT    3240

CTTTTGGAAT AGCTTCATAT GCTCAAGTGT CTTCTTGTCC GACTTCGTTA ACATTACAAT    3300

GTCAATATAG CAAATTGTTT GTGACTGTAT CAACGCGAAC TTCCACTTGT ATTTCTTGAA    3360

CTTCGTAATT AGTTTGTTAA TGCAGTATAA GAACTATTGG TACTACGTAA TAACTTACAG    3420

TATTTTCTTC TTAACTTACT TTAATTTTTC TTTAAGTTTA GACTTGCTGA CAGAAATTAA    3480

CTTCGTCTTT AACTTCTTTA ATTTTAACTG TTTCTTCAAT ACCACGGATC ACTTCTTCAA    3540

TAAAATTCAT ACTGTGCAGT ACCTATATAA TTTGCATGAA GATAAGCATC GAAATTACGA    3600

TCGCCACAAC TTCTATAACC AAATTTTCTA CCACTGTCAA ATGAATTTGT AGTTCTTCAT    3660

TTATGCGTTC TATGGCATGA TCATAAATGT TTATTTCCAG CAATAGATAA ATATGGTCAA    3720

GTATTTAATG CTCTATAAGC AACCTTTCTT AACCCCGTTG TACATAGTGT TTATCAAGGA    3780

TAGCTTCTTC TACTTCACCA ATAATTACAG ATATTACTTT TCCTGAAATT ATGACTACGT    3840

AAAATACAAA AACGCTGAGT TTTACCGTAC TAATTCTTTT CATGTCACGG AGATAAATTT    3900

TGTTGCGCAA AATTATTTGG AAATTAACGT TGATTTCAAT TTCTTTTACT ACTAAACTAA    3960

TCACAATACG CGAAACTTTT TCTAGTTAAT TAATGGCATT AATGTTTATT TCCATACAGT    4020

AATTGCATAT TATGTTCACT TGATAGTCTA TGACCTAATT CCCGCCGACC ACAATTTAGT    4080

TATTTAGAAT TTCAACTTCT AAAGCAACAA TACTGTCTTC CACAAAGACT TTTACTATGA    4140

TATAACTACC GGTGTGTTGC GCCGAGCAAT TTTGCATAAT CAAAATTTTA GAATGTTCAA    4200

CGATTTTCTC GTGTTGCACC TTATTGAAAT AATTTTCTTA ATTTCTTTTT AGGTGTAGCA    4260

TATCATCGAC GTGTACATCA CTGTCCACTT GTATCAGTTA TATGTAATAT AAGTTTTAGT    4320

TTGCTTCTTG TACCAAATTA ATTACTATAA GTATTTAGAC TTGTTATATG TTTACCGAGT    4380

AAGTAACATC TATGTCTACT AAAACCACTT CATTATCTGT ACATATAATC GATTTTTGAT    4440

ATACGTTAGT GCTTTAATTT ACTATTTTAT GTCATTACAA TTTAAAACTG ATTTAAGTTC    4500

CCTAAATATA ATTTACGACT GGTTCATGAA TAGCAATTTA ATCGCTATGC CTTAGGCGCC    4560

TTAAG                                                               4565
```

(2) INFORMATION FOR SEQ ID NO:3:

(i) SEQUENCE CHARACTERISTICS:
        (A) LENGTH: 800 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Ser Glu Ile Ile Gln Asp Leu Ser Leu Glu Asp Val Leu Gly Asp
1               5                   10                  15
```

-continued

```
Arg Phe Gly Arg Tyr Ser Lys Tyr Ile Ile Gln Glu Arg Ala Leu Pro
            20                  25                  30

Asp Val Arg Asp Gly Leu Lys Pro Val Gln Arg Arg Ile Leu Tyr Ala
            35                  40                  45

Met Tyr Ser Ser Gly Asn Thr His Asp Lys Asn Phe Arg Lys Ser Ala
 50                      55                  60

Lys Thr Val Gly Asp Val Ile Gly Gln Tyr His Pro His Gly Asp Ser
 65                  70                  75                  80

Ser Val Tyr Glu Ala Met Val Arg Leu Ser Gln Asp Trp Lys Leu Arg
                 85                  90                  95

His Val Leu Ile Glu Met His Gly Asn Asn Gly Ser Ile Asp Asn Asp
             100                 105                 110

Pro Pro Ala Ala Met Arg Tyr Thr Glu Ala Lys Leu Ser Leu Leu Ala
             115                 120                 125

Glu Glu Leu Leu Arg Asp Ile Asn Lys Glu Thr Val Ser Phe Ile Pro
130                 135                 140

Asn Tyr Asp Asp Thr Thr Leu Glu Pro Met Val Leu Pro Ser Arg Phe
145                 150                 155                 160

Pro Asn Leu Leu Val Asn Gly Ser Thr Gly Ile Ser Ala Gly Tyr Ala
                 165                 170                 175

Thr Asp Ile Pro Pro His Asn Leu Ala Glu Val Ile Gln Ala Thr Leu
             180                 185                 190

Lys Tyr Ile Asp Asn Pro Asp Ile Thr Val Asn Gln Leu Met Lys Tyr
             195                 200                 205

Ile Lys Gly Pro Asp Phe Pro Thr Gly Gly Ile Ile Gln Gly Ile Asp
210                 215                 220

Gly Ile Lys Lys Ala Tyr Glu Ser Gly Lys Gly Arg Ile Ile Val Arg
225                 230                 235                 240

Ser Lys Val Glu Glu Glu Thr Leu Arg Asn Gly Arg Lys Gln Leu Ile
                 245                 250                 255

Ile Thr Glu Ile Pro Tyr Glu Val Asn Lys Gly Ser Leu Val Lys Arg
             260                 265                 270

Ile Asp Glu Leu Arg Ala Asp Lys Lys Val Asp Gly Ile Val Glu Val
             275                 280                 285

Arg Asp Glu Thr Asp Arg Thr Gly Leu Arg Ile Ala Ile Glu Leu Lys
290                 295                 300

Lys Asp Val Asn Ser Glu Ser Ile Lys Asn Tyr Leu Tyr Lys Asn Ser
305                 310                 315                 320

Asp Leu Gln Ile Ser Tyr Asn Phe Asn Met Val Ala Ile Ser Asp Gly
                 325                 330                 335

Arg Pro Lys Leu Met Gly Ile Arg Gln Ile Ile Asp Ser Tyr Leu Asn
             340                 345                 350

His Gln Ile Glu Val Val Ala Asn Arg Thr Lys Phe Glu Leu Asp Asn
             355                 360                 365

Ala Glu Lys Arg Met His Ile Val Glu Gly Leu Ile Lys Ala Leu Ser
370                 375                 380

Ile Leu Asp Lys Val Ile Glu Leu Ile Arg Ser Ser Lys Asn Lys Arg
385                 390                 395                 400

Asp Ala Lys Glu Asn Leu Ile Glu Val Tyr Glu Phe Thr Glu Glu Gln
                 405                 410                 415

Ala Glu Ala Ile Val Met Leu Gln Leu Tyr Arg Leu Thr Asn Thr Asp
             420                 425                 430

Ile Val Ala Leu Glu Gly Glu His Lys Glu Leu Glu Ala Leu Ile Lys
             435                 440                 445
```

```
Gln Leu Arg His Ile Leu Asp Asn His Asp Ala Leu Leu Asn Val Ile
    450                 455                 460

Lys Glu Glu Leu Asn Glu Ile Lys Lys Phe Lys Ser Glu Arg Leu
465                 470                 475                 480

Ser Leu Ile Glu Ala Glu Ile Glu Glu Ile Lys Ile Asp Lys Glu Val
                485                 490                 495

Met Val Pro Ser Glu Glu Val Ile Leu Ser Met Thr Arg His Gly Tyr
            500                 505                 510

Ile Lys Arg Thr Ser Ile Arg Ser Phe Asn Ala Ser Gly Val Glu Asp
        515                 520                 525

Ile Gly Leu Lys Asp Gly Asp Ser Leu Leu Lys His Gln Glu Val Asn
    530                 535                 540

Thr Gln Asp Thr Val Leu Val Phe Thr Asn Lys Gly Arg Tyr Leu Phe
545                 550                 555                 560

Ile Pro Val His Lys Leu Arg Asp Ile Arg Trp Lys Glu Leu Gly Gln
                565                 570                 575

His Val Ser Gln Ile Val Pro Ile Glu Glu Asp Glu Val Val Ile Asn
            580                 585                 590

Val Tyr Asn Glu Lys Asp Phe Asn Thr Asp Ala Phe Tyr Val Phe Ala
        595                 600                 605

Thr Gln Asn Gly Met Ile Lys Lys Ser Thr Val Pro Leu Phe Lys Thr
    610                 615                 620

Thr Arg Pro Asn Lys Pro Leu Ile Ala Thr Lys Val Lys Glu Asn Asp
625                 630                 635                 640

Asp Leu Ile Ser Val Met Arg Phe Glu Lys Asp Gln Leu Ile Thr Val
                645                 650                 655

Ile Thr Asn Lys Gly Met Ser Leu Thr Tyr Asn Thr Ser Glu Leu Ser
            660                 665                 670

Asp Thr Gly Leu Arg Ala Ala Gly Val Lys Ser Ile Asn Leu Lys Val
        675                 680                 685

Glu Asp Phe Val Val Met Thr Glu Gly Val Ser Glu Asn Asp Thr Ile
    690                 695                 700

Leu Met Ala Thr Gln Arg Gly Ser Leu Lys Arg Ile Ser Phe Lys Ile
705                 710                 715                 720

Leu Gln Val Ala Lys Arg Ala Gln Arg Gly Ile Thr Leu Leu Lys Glu
                725                 730                 735

Leu Lys Lys Asn Pro His Arg Ile Val Ala Ala His Val Thr Gly
            740                 745                 750

Glu His Ser Gln Tyr Thr Leu Tyr Ser Lys Ser Asn Glu Glu His Gly
        755                 760                 765

Leu Ile Asn Asp Ile His Lys Ser Glu Gln Tyr Thr Asn Gly Ser Phe
    770                 775                 780

Ile Val Asp Thr Asp Asp Phe Gly Glu Val Ile Asp Met Tyr Ile Ser
785                 790                 795                 800

(2) INFORMATION FOR SEQ ID NO:4:

(i) SEQUENCE CHARACTERISTICS:
        (A) LENGTH: 2402 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:
```

```
GTGAGTGAAA TAATTCAAGA TTTATCACTT GAAGATGTTT TAGGTGATCG CTTTGGAAGA      60

TATAGTAAAT ATATTATTCA AGAGCGTGCA TTGCCAGATG TTCGTGATGG TTTAAAACCA     120

GTACAACGTC GTATTTTATA CGCAATGTAT TCAAGTGGTA ATACACACGA TAAAAATTTC    180

CGTAAAAGTG CGAAAACAGT CGGTGATGTT ATTGGTCAAT ATCATCCACA TGGAGACTCC    240

TCAGTGTACG AAGCAATGGT CCGTTTAAGT CAAGACTGGA AGTTACGACA TGTCTTAATA    300

GAAATGCATG GTAATAATGG TAGTATCGAT AATGATCCGC CAGCGGCAAT GCGTTACACT    360

GAAGCTAAGT TAAGCTTACT AGCTGAAGAG TTATTACGTG ATATTAATAA AGAGACAGTT    420

TCTTTCATTC CAAACTATGA TGATACGACA CTCGAACCAA TGGTATTGCC ATCAAGATTT    480

CCTAACTTAC TAGTGAATGG TTCTACAGGT ATATCTGCAG GTTACGCGAC AGATATACCA    540

CCACTAATTT AGCTGAAGTG ATTCAAGCAA CACTTAAATA TATTGATAAT CCGGATATTA    600

TAGTCAATCA ATTAATGAAA TATATTAAAG GTCCTGATTT TCCAACTGGT GGTATTATTC    660

AAGGTATTGA TGGTATTAAA AAAGCTTATG AATCAGGTAA AGGTAGAATT ATAGTTCGTT    720

CTAAAGTTGA AGAAGAAATT TTACGCAATG GACGTAAACA GTTAATTATT ACTGAAATTC    780

CATATGAAGT GAACAAAGGT AGCTTAGTAA ACGTATCGA TGAATTACGT GCTGACAAAA    840

AAGTCGATGG TATCGTTGAA GTACGTGATG AAACTGATAG AACTGGTTTA CGAATAGCAA    900

TTGAATTGAA AAAAGATGTG AACAGTGAAT CAATCAAAAA TTATCTTTAT AAAAACTCTG    960

ATTTACAGAT TCATATAAT TTCAACATGG TCGCTATTAG TGATGGTCGT CCAAAATTGA   1020

TGGGTATTCG TCAAATTATA GATAGTTATT TGAATCATCA AATTGAGGTT GTTGCAAATA   1080

GAACGAAGTT TGAATTAGAT AATGCTGAAA AACGTATGCA TATCGTTGAA GGTTTGATTA   1140

AAGCGTTGTC AATTTTAGAT AAAGTAATCG AATTGATTCG TAGCTCTAAA AACAAGCGTG   1200

ACGCTAAAGA AAACCTTATC GAAGTATACG AGTTCACAGA AGAACAGGCT GAAGCAATTG   1260

TAATGTTACA GTTATATCGT TTAACAAACA CTGACATAGT TGCGCTTGAA GGTGAACATA   1320

AAGAACTTGA AGCATTAATC AAACAATTAC GTCATATTCT TGATAACCAT GATGCATTAT   1380

TGAATGTCAT AAAAGAAGAA TTGAATGAAA TTAAAAAGAA ATTCAAATCT GAACGACTGT   1440

CTTTAATTGA AGCAGAAATT GAAGAAATTA AAATTGACAA AGAAGTTATG GTGCCTAGTG   1500

AAGAAGTTAT TTTAAGTATG ACACGTCATG GATATATTAA ACGTACTTCT ATTCGTAGCT   1560

TTAATGCTAG CGGTGTTGAA GATATTGGTT TAAAAGATGG TGACAGTTTA CTTAAACATC   1620

AAGAAGTAAA TACGCAAGAT ACCGTACTAG TATTTACAAA TAAAGGTCGT TATCTATTTA   1680

TACCAGTTCA TAAATTACGA GATATTCGTT GGAAAGAATT GGGGCAACAT GTATCACAAA   1740

TAGTTCCTAT CGAAGAAGAT GAAGTGGTTA TTAATGTTTA TAATGAAAAG GACTTTAATA   1800

CTGATGCATT TTATGTTTTT GCGACTCAAA ATGGCATGAT TAAGAAAAGT ATAGTGCCTC   1860

TATTTAAAAC AACGCGTTTT AATAAACCTT TAATTGCAAC TAAAGTTAAA GAAAATGATG   1920

ATTTGATTAG TGTTATGCGT TTTGAAAAAG ATCAATTAAT TACCGTAATT ACAAATAAAG   1980

GTATGTCATT AACGTATAAT ACAAGTGAAC TATCAGATAC TGGATTAAGG GCGGCTGGTG   2040

TTAAATCAAT AAATCTTAAA GTTGAAGATT TCGTTGTTAT GACAGAAGGT GTTTCTGAAA   2100

ATGATACTAT ATTGATGGCC ACACAACGCG GCTCGTTAAA ACGTATTAGT TTTAAAATCT   2160

TACAAGTTGC TAAAAGAGCA CAACGTGGAA TAACTTTATT AAAAGAATTA AAGAAAAATC   2220

CACATCGTAT AGTAGCTGCA CATGTAGTGA CAGGTGAACA TAGTCAATAT ACATTATATT   2280

CAAAATCAAA CGAAGAACAT GGTTTAATTA ATGATATTCA TAAATCTGAA CAATATACAA   2340

ATGGCTCATT CATTGTAGAT ACAGATGATT TTGGTGAAGT AATAGACATG TATATTAGCT   2400
```

AA                                                                                              2402

(2) INFORMATION FOR SEQ ID NO:5:

(i) SEQUENCE CHARACTERISTICS:
        (A) LENGTH: 663 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Asn Lys Gln Asn Asn Tyr Ser Asp Asp Ser Ile Gln Val Leu Glu
  1               5                  10                  15

Gly Leu Glu Ala Val Arg Lys Arg Pro Gly Met Tyr Ile Gly Ser Thr
             20                  25                  30

Asp Lys Arg Gly Leu His His Leu Val Tyr Glu Ile Val Asp Asn Ser
         35                  40                  45

Val Asp Glu Val Leu Asn Gly Tyr Gly Asn Glu Ile Asp Val Thr Ile
     50                  55                  60

Asn Lys Asp Gly Ser Ile Ser Ile Glu Asp Asn Gly Arg Gly Met Pro
 65                  70                  75                  80

Thr Gly Ile His Lys Ser Gly Lys Pro Thr Val Glu Val Ile Phe Thr
                 85                  90                  95

Val Leu His Ala Gly Gly Lys Phe Gly Gln Gly Gly Tyr Lys Thr Ser
            100                 105                 110

Gly Gly Leu His Gly Val Gly Ala Ser Val Val Asn Ala Leu Ser Glu
        115                 120                 125

Trp Leu Glu Val Glu Ile His Arg Asp Gly Asn Ile Tyr His Gln Ser
    130                 135                 140

Phe Lys Asn Gly Gly Ser Pro Ser Ser Gly Leu Val Lys Lys Gly Lys
145                 150                 155                 160

Thr Lys Lys Thr Gly Thr Lys Val Thr Phe Lys Pro Asp Asp Thr Ile
                165                 170                 175

Phe Lys Ala Ser Thr Ser Phe Asn Phe Asp Val Leu Ser Glu Arg Leu
            180                 185                 190

Gln Glu Ser Ala Phe Leu Leu Lys Asn Leu Lys Ile Thr Leu Asn Asp
        195                 200                 205

Leu Arg Ser Gly Lys Glu Arg Gln Glu His Tyr His Tyr Glu Glu Gly
    210                 215                 220

Ile Lys Glu Phe Val Ser Tyr Val Asn Glu Gly Lys Glu Val Leu His
225                 230                 235                 240

Asp Val Ala Thr Phe Ser Gly Glu Ala Asn Gly Ile Glu Val Asp Val
                245                 250                 255

Ala Phe Gln Tyr Asn Asp Gln Tyr Ser Glu Ser Ile Leu Ser Phe Val
            260                 265                 270

Asn Asn Val Arg Thr Lys Asp Gly Gly Thr His Glu Val Gly Phe Lys
        275                 280                 285

Thr Ala Met Thr Arg Val Phe Asn Asp Tyr Ala Arg Arg Ile Asn Glu
    290                 295                 300

Leu Lys Thr Lys Asp Lys Asn Leu Asp Gly Asn Asp Ile Arg Glu Gly
305                 310                 315                 320

Leu Thr Ala Val Val Ser Val Arg Ile Pro Glu Glu Leu Leu Gln Phe
                325                 330                 335

Glu Gly Gln Thr Lys Ser Lys Leu Gly Thr Ser Glu Ala Arg Ser Ala
            340                 345                 350
```

```
Val Asp Ser Val Val Ala Asp Lys Leu Pro Phe Tyr Leu Glu Glu Lys
            355                 360                 365
Gly Gln Leu Ser Lys Ser Leu Val Lys Ala Ile Lys Ala Gln Gln
        370                 375                 380
Ala Arg Glu Ala Ala Arg Lys Ala Arg Glu Asp Ala Arg Ser Gly Lys
385                 390                 395                 400
Lys Asn Lys Arg Lys Asp Thr Leu Leu Ser Gly Lys Leu Thr Pro Ala
                405                 410                 415
Gln Ser Lys Asn Thr Glu Lys Asn Glu Leu Tyr Leu Val Glu Gly Asp
            420                 425                 430
Ser Ala Gly Gly Ser Ala Lys Leu Gly Arg Asp Arg Lys Phe Gln Ala
            435                 440                 445
Ile Leu Pro Leu Arg Gly Lys Val Ile Asn Thr Glu Lys Ala Arg Leu
        450                 455                 460
Glu Asp Ile Phe Lys Asn Glu Ile Asn Thr Ile Ile His Thr Ile
465                 470                 475                 480
Gly Ala Gly Val Gly Thr Asp Phe Lys Ile Glu Asp Ser Asn Tyr Asn
                485                 490                 495
Arg Val Ile Ile Met Thr Asp Ala Asp Thr Asp Gly Ala His Ile Gln
            500                 505                 510
Val Leu Leu Leu Thr Phe Phe Lys Tyr Met Lys Pro Leu Val Gln
        515                 520                 525
Ala Gly Arg Val Phe Ile Ala Leu Pro Pro Leu Tyr Lys Leu Glu Lys
        530                 535                 540
Gly Lys Gly Lys Thr Lys Arg Val Glu Tyr Ala Trp Thr Asp Glu Glu
545                 550                 555                 560
Leu Asn Lys Leu Gln Lys Glu Leu Gly Lys Gly Phe Thr Leu Gln Arg
                565                 570                 575
Tyr Lys Gly Leu Gly Glu Met Asn Pro Glu Gln Leu Trp Glu Thr Thr
            580                 585                 590
Met Asn Pro Glu Thr Arg Thr Leu Ile Arg Val Gln Val Glu Asp Glu
        595                 600                 605
Val Arg Ser Ser Lys Arg Val Thr Thr Leu Met Gly Asp Lys Val Gln
610                 615                 620
Pro Arg Arg Glu Trp Ile Glu Lys His Val Glu Phe Gly Met Gln Glu
625                 630                 635                 640
Asp Gln Ser Ile Leu Asp Asn Ser Glu Val Gln Val Leu Glu Asn Asp
                645                 650                 655
Gln Phe Asp Glu Glu Glu Ile
            660
```

(2) INFORMATION FOR SEQ ID NO:6:

(i) SEQUENCE CHARACTERISTICS:
        (A) LENGTH: 1992 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
ATGAATAAAC AAAATAATTA TTCAGATGAT TCAATACAGG TTTTAGAGGG GTTAGAAGCA      60

GTTCGTAAAA GACCTGGTAT GTATATTGGA TCAACTGATA ACGGGGATT ACATCATCTA     120

GTATATGAAA TTGTCGATAA CTCCGTCGAT GAAGTATTGA ATGGTTACGG TAACGAAATA     180
```

-continued

```
GATGTAACAA TTAATAAAGA TGGTAGTATT TCTATAGAAG ATAATGGACG TGGTATGCCA    240

ACAGGTATAC ATAAATCAGG TAAACCGACA GTCGAAGTTA TCTTTACTGT TTTACATGCA    300

GGAGGTAAAT TTGGACAAGG TGGCTATAAA ACTTCAGGTG GTCTTCACGG CGTTGGTGCT    360

TCAGTGGTAA ATGCATTGAG TGAATGGCTT GAAGTTGAAA TCCATCGAGA TGGTAATATA    420

TATCATCAAA GTTTTAAAAA CGGTGGTTCG CCATCTTCAG GTTTAGTGAA AAAAGGTAAA    480

ACTAAGAAAA CAGGTACCAA AGTAACATTT AAACCTGATG ACACAATTTT TAAAGCATCT    540

ACATCATTTA ATTTTGATGT TTTAAGTGAA CGACTACAAG AGTCTGCGTT CTTATTGAAA    600

AATTTAAAAA TAACGCTTAA TGATTTACGC AGTGGTAAAG AGCGTCAAGA GCATTACCAT    660

TATGAAGAAG GAATCAAAGA GTTTGTTAGT TATGTCAATG AAGGAAAAGA AGTTTTGCAT    720

GACGTGGCTA CATTTTCAGG TGAAGCAAAT GGTATAGAGG TAGACGTAGC TTTCCAATAT    780

AATGATCAAT ATTCAGAAAG TATTTTAAGT TTTGTAAATA ATGTACGTAC TAAAGATGGT    840

GGTACACATG AAGTTGGTTT TAAAACAGCA ATGACACGCG TATTTAATGA TTATGCACGT    900

CGTATTAATG AACTTAAAAC AAAAGATAAA AACTTAGATG GTAATGATAT TCGTGAAGGT    960

TTAACAGCTG TTGTGTCTGT TCGTATTCCA GAAGAATTAT TGCAATTTGA AGGACAAACG   1020

AAATCTAAAT TGGGTACTTC TGAAGCTAGA AGTGCTGTTG ATTCAGTTGT TGCAGACAAA   1080

TTGCCATTCT ATTTAGAAGA AAAAGGACAA TTGTCTAAAT CACTTGTGAA AAAAGCGATT   1140

AAAGCACAAC AAGCAAGGGA AGCTGCACGT AAAGCTCGTG AAGATGCTCG TTCAGGTAAG   1200

AAAAACAAGC GTAAAGACAC TTTGCTATCT GGTAAATTAA CACCTGCACA AGTAAAAAC   1260

ACTGAAAAAA ATGAATTGTA TTTAGTCGAA GGTGATTCTG CGGGAGGTTC AGCAAAACTT   1320

GGACGAGACC GCAAATTCCA AGCGATATTA CCATTACGTG GTAAGGTAAT TAATACAGAG   1380

AAAGCACGTC TAGAAGATAT TTTTAAAAAT GAAGAAATTA ATACAATTAT CCACACAATC   1440

GGGGCAGGCG TTGGTACTGA CTTTAAAATT GAAGATAGTA ATTATAATCG TGTAATTATT   1500

ATGACTGATG CTGATACTGA TGGTGCGCAT ATTCAAGTGC TATTGTTAAC ATTCTTCTTC   1560

AAATATATGA AACCGCTTGT TCAAGCAGGT CGTGTATTTA TTGCTTTACC TCCACTTTAT   1620

AAATTGGAAA AAGGTAAAGG CAAAACAAAG CGAGTTGAAT ACGCTTGGAC AGACGAAGAG   1680

CTTAATAAAT TGCAAAAAGA ACTTGGTAAA GGCTTCACGT TACAACGTTA CAAAGGTTTG   1740

GGTGAAATGA ACCCTGAACA ATTATGGGAA ACGACGATGA ACCCAGAAAC ACGAACTTTA   1800

ATTCGTGTAC AAGTTGAAGA TGAAGTGCGT TCATCTAAAC GTGTAACAAC ATTAATGGGT   1860

GACAAAGTAC AACCTAGACG TGAATGGATT GAAAAGCATG TTGAGTTTGG TATGCAAGAG   1920

GACCAAAGTA TTTTAGATAA TTCTGAAGTA CAAGTGCTTG AAAATGATCA ATTTGATGAG   1980

GAGGAAATCT AG                                                      1992
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
GCGCGAATTC GATGGWYTWA AACCWGTWCA                                     30
```

(2) INFORMATION FOR SEQ ID NO:8:

```
    (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGCGAAGCTT TTCWGTATAW CKCATWGCWG C                                   31

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCGCGAATTC TWCATGCWGG WGGWAAATT                                      29

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCGAAGCTT WCCWCCWGCW GAATCWCCTT C                                   31

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ala Ala Met Arg Tyr Thr Glu
1               5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Tyr His Pro His Gly Asp Ser
1               5

(2) INFORMATION FOR SEQ ID NO:13:

(i) SEQUENCE CHARACTERISTICS:
        (A) LENGTH: 29 base pairs
        (B) TYPE: nucleic acid
```

```
        (C) STRANDEDNESS: single
        (D) TOPOLOGY: linear (ii) MOLECULE TYPE: cDNA (xi) SEQUENCE DESCRIPTION: SEQ ID NO:13:

GGCGGATCCC ATATGGCTGA ATTACCTCA                                         29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGCGGAATTC GACGGCTCTC TTTCATTAC                                         29

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GGCCGGATCC CATATGAGTG AAATAATTCA AGATT                                  35

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGCCGAATTC TAATAATTAA CTGTTTACGT CC                                     32

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGCCGAGCTC CAATTCTTCT TTTATGACAT TC                                     32
```